US010354436B2

United States Patent
Akimoto et al.

(10) Patent No.: US 10,354,436 B2
(45) Date of Patent: Jul. 16, 2019

(54) IMAGE PROCESSING APPARATUS, IMAGE PROCESSING SYSTEM AND IMAGE PROCESSING APPARATUS OPERATION METHOD

(71) Applicant: OLYMPUS CORPORATION, Tokyo (JP)

(72) Inventors: Syunya Akimoto, Kawasaki (JP); Junichi Onishi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/128,919

(22) Filed: Sep. 12, 2018

(65) Prior Publication Data

US 2019/0012827 A1 Jan. 10, 2019

Related U.S. Application Data

(63) Continuation of application No. PCT/JP2016/079988, filed on Oct. 7, 2016.

(30) Foreign Application Priority Data

Mar. 15, 2016 (JP) ................................ 2016-051274

(51) Int. Cl.
*G06T 7/55* (2017.01)
*G06T 15/20* (2011.01)
(Continued)

(52) U.S. Cl.
CPC ........ *G06T 15/205* (2013.01); *A61B 1/00009* (2013.01); *G02B 23/24* (2013.01);
(Continued)

(58) Field of Classification Search
None
See application file for complete search history.

(56) References Cited

U.S. PATENT DOCUMENTS 7,728,868 B2 * 6/2010 Razzaque ............ A61B 1/0005 348/77
8,585,598 B2 * 11/2013 Razzaque .......... A61B 18/1477 600/439
(Continued)

FOREIGN PATENT DOCUMENTS

EP 2030558 A1 3/2009
EP 2090215 A1 8/2009
(Continued)

OTHER PUBLICATIONS

International Search Report dated Dec. 13, 2016 issued in PCT/JP2016/079988.

*Primary Examiner* — Said Broome
(74) *Attorney, Agent, or Firm* — Scully, Scott, Murphy & Presser, P.C.

(57) ABSTRACT

An image processing apparatus includes a processor including hardware, wherein the processor is configured to: construct first and second pieces of three-dimensional image data based on two different subject images received; arrange first and second three-dimensional shapes included in the first and second pieces of three-dimensional image data at positions corresponding to pieces of image pickup position information; calculate a deviation angle based on at least one of a degree of similarity between hues, a degree of similarity between textures and a degree of similarity between edges, and correct the deviation angle and arrange the first and second three-dimensional shapes in three-dimensional space to generate a three-dimensional shape image.

9 Claims, 18 Drawing Sheets

(51) Int. Cl.

| | |
|---|---|
| ***G02B 23/24*** | (2006.01) |
| ***H04N 7/18*** | (2006.01) |
| ***G06T 7/00*** | (2017.01) |
| ***A61B 1/00*** | (2006.01) |

(52) U.S. Cl.

CPC .................. *G06T 7/55* (2017.01); *G06T 7/97* (2017.01); *H04N 7/18* (2013.01)

(56) References Cited

U.S. PATENT DOCUMENTS

| | | | | |
|---|---|---|---|---|
| 2005/0085718 | A1* | 4/2005 | Shahidi .................... | A61B 1/04<br>600/424 |
| 2006/0052708 | A1 | 3/2006 | Iddan et al. | |
| 2009/0207241 | A1 | 8/2009 | Igarashi et al. | |
| 2010/0049033 | A1 | 2/2010 | Kawano et al. | |

FOREIGN PATENT DOCUMENTS

| | | | |
|---|---|---|---|
| JP | H07-262370 | A | 10/1995 |
| JP | 2006-527012 | A | 11/2006 |
| JP | 2007-159641 | A | 6/2007 |
| JP | 2008-119253 | A | 5/2008 |
| JP | 5354494 | B2 | 11/2013 |
| WO | WO 2004/096008 | A2 | 11/2004 |
| WO | WO 2007/139187 | A1 | 12/2007 |
| WO | WO 2008/059773 | A1 | 5/2008 |

* cited by examiner

5
IMAGE PROCESSING APPARATUS
21
IMAGE INPUTTING PORTION
22
THREE-DIMENSIONAL IMAGE CONSTRUCTING PORTION
23
POSITIONAL RELATIONSHIP CALCULATING PORTION
26
PERIPHERAL IMAGE GENERATING PORTION
27
CHARACTERISTIC PART DETECTING PORTION
28
SIMILARITY DEGREE CALCULATING PORTION
25
STORAGE PORTION
24
THREE-DIMENSIONAL SHAPE IMAGE GENERATING PORTION
29
INPUTTING PORTION

IMAGE PROCESSING APPARATUS, IMAGE PROCESSING SYSTEM AND IMAGE PROCESSING APPARATUS OPERATION METHOD

CROSS REFERENCE TO RELATED APPLICATION

This application is a continuation application of PCT/JP2016/079988 filed on Oct. 7, 2016 and claims benefit of Japanese Application No. 2016-051274 filed in Japan on Mar. 15, 2016, the entire contents of which are incorporated herein by this reference.

BACKGROUND OF THE INVENTION

1. Field of the Invention

The present invention relates to an image processing apparatus for generating a three-dimensional shape image from a plurality of two-dimensional subject images, an image processing system and an image processing apparatus operation method.

2. Description of the Related Art

Conventionally, a technique of constructing a three-dimensional shape from two-dimensional images has been proposed. Only a partial three-dimensional shape corresponding to the two-dimensional image corresponding to the one frame can be constructed as a three-dimensional shape that can be constructed from a two-dimensional image corresponding to one frame. Therefore, a technique of constructing a three-dimensional shape of an entire target organ using two-dimensional images corresponding to a plurality of frames obtained by observing the entire organ is also proposed.

For example, Japanese Patent No. 5354494 describes a three-dimensional image generation apparatus generating a three-dimensional image (for example, a virtual endoscopic image) having a high resolution and is provided with color information. More specifically, in the technique described in the above official gazette, only pixels, for example, on a circular test line are extracted and one-dimensionally developed, for each of a plurality of frame images. Furthermore, by combining a plurality of one-dimensionally developed pixel strings, a two-dimensional image of an inner wall of a tubular structure being planarly developed is generated. The generated two-dimensional image is divided in a grid shape. Three-dimensional coordinates (x, y, z) (model space coordinates) are calculated based on luminance information on each coordinate on the two-dimensional image to generate a three-dimensional model. Then, by attaching texture of the two-dimensional image to the three-dimensional model based on two-dimensional coordinates and the three-dimensional coordinates, a three-dimensional model is generated.

In order to accurately generate the two-dimensional image of an inner wall of a tubular structure planarly developed in such a technique, it is necessary to grasp a positional relationship among the plurality of one-dimensionally developed pixel strings, and 6-degree-of-freedom information about an endoscope to acquire the frame images, that is, a three-dimensional position (three-dimensional translational-degree-of-freedom information), a rotational degree of freedom around an optical axis of an optical system of the endoscope, and each of pieces of information about rotational degrees of freedom around two axes orthogonal to the optical axis are required.

SUMMARY OF THE INVENTION

An image processing apparatus according to an aspect of the present invention includes a processor including hardware. The processor is configured to receive a two-dimensional subject image obtained by picking up an image of a subject, and a piece of image pickup position information including three-dimensional xyz coordinates of an endoscope distal end portion when the subject image is picked up and rotation angles around an x axis and a y axis perpendicular to a z axis, where the z axis is an optical axis of an objective lens mounted on an endoscope insertion portion; construct a first piece of three-dimensional image data showing a three-dimensional shape of a first area of the subject and a second piece of three-dimensional image data showing a three-dimensional shape of a second area of the subject, based on two different subject images, where each of the subject images is the subject image described above; arrange the three-dimensional shape of the first area included in the first piece of three-dimensional image data and the three-dimensional shape of the second area included in the second piece of three-dimensional image data at positions corresponding to respective pieces of image pickup position information, where each of the pieces of image pickup position information is the piece of image pickup position information described above, and calculate a deviation angle indicating an amount of angle deviation around a rotation axis, where the rotation axis is in an image pickup direction of the subject images determined based on the pieces of image pickup position information, based on at least one of a degree of similarity between pieces of hue information that the respective pieces of three-dimensional image data include, a degree of similarity between pieces of texture information that the respective pieces of three-dimensional image data include, and a degree of similarity between pieces of information about edges showing shapes of facing parts of the three-dimensional shapes of the first area and the second area; and correct the deviation angle between the three-dimensional shapes of the first area and the second area arranged at positions corresponding to the respective pieces of image pickup position information and arrange the three-dimensional shapes in three-dimensional space to generate a three-dimensional shape image.

An image processing system according to an aspect of the present invention includes: an endoscope configured to pick up an image of a subject and generate a two-dimensional subject image; and the image processing apparatus described above. The two-dimensional subject image received by the processor is the two-dimensional subject image generated by the endoscope.

An image processing apparatus operation method according to an aspect of the present invention includes steps of: receiving a two-dimensional subject image obtained by picking up an image of a subject, and a piece of image pickup position information including three-dimensional xyz coordinates of an endoscope distal end portion when the subject image is picked up and rotation angles around an x axis and a y axis perpendicular to a z axis, where the z axis is an optical axis of an objective lens mounted on an endoscope insertion portion; constructing a first piece of three-dimensional image data showing a three-dimensional shape of a first area of the subject and a second piece of three-dimensional image data showing a three-dimensional shape of a second area of the subject, based on two different subject images, where each of the subject images is the subject image described above; arranging the three-dimensional shape of the first area included in the first piece of three-dimensional image data and the three-dimensional shape of the second area included in the second piece of three-dimensional image data at positions corresponding to respective pieces of image pickup position information, each of the pieces of image pickup position information is the piece of image pickup position information described above, and calculating a deviation angle indicating an amount of angle deviation around a rotation axis, where the rotation axis is in an image pickup direction of the subject images determined based on the pieces of image pickup position information, based on at least one of a degree of similarity between pieces of hue information that the respective pieces of three-dimensional image data include, a degree of similarity between pieces of texture information that the respective pieces of three-dimensional image data include, and a degree of similarity between pieces of information about edges showing shapes of facing parts of the three-dimensional shapes of the first area and the second area; and correcting the deviation angle between the three-dimensional shapes of the first area and the second area arranged at the positions corresponding to respective pieces of image pickup position information, and arranging the three-dimensional shapes in three-dimensional space to generate a three-dimensional shape image.

DETAILED DESCRIPTION OF THE PREFERRED EMBODIMENTS

Embodiments of the present invention will be described below with reference to drawings.

[First Embodiment]

Figure 1:
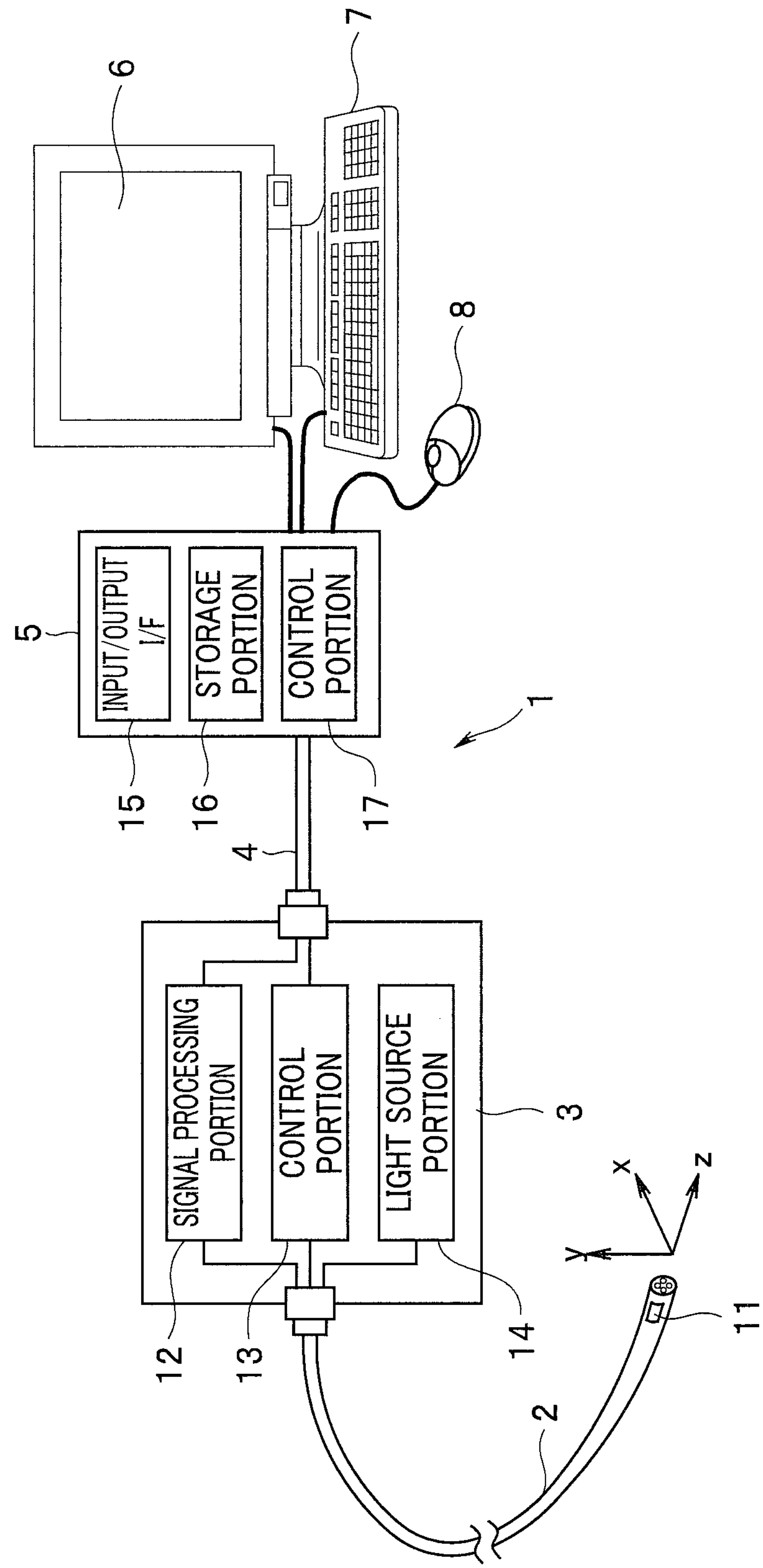
FIG. 1 is a diagram showing a configuration of an image processing system in a first embodiment of the present invention.

FIGS. 1 to 16 show a first embodiment of the present invention, and FIG. 1 is a diagram showing a configuration of an image processing system 1.

The image processing system 1 of the present embodiment is provided with an endoscope 2, a video processor 3, a cable 4, an image processing apparatus 5, a monitor 6, a keyboard 7 and a mouse 8 and is provided with a function as an observation support apparatus for generating and displaying a three-dimensional shape image of a subject from two-dimensional images obtained by picking up an image of the subject.

The endoscope 2 is, for example, an image pickup apparatus configured including an image pickup system including an objective lens, an image pickup device and the like, and an illumination system including an illumination lens and optical fibers. The endoscope 2 is, however, not limited to the above configuration. For example, the illumination system may include an LED or the like, and any other configuration that can be taken for an endoscope may be adopted. Here, the endoscope 2 can be either a medical endoscope or an industrial endoscope.

The endoscope 2 is provided with a 5-degree-of-freedom sensor (hereinafter referred to as a 5D sensor) 11 in a distal end portion in which an image pickup system of an insertion portion is provided. When an optical axis of the objective lens in the insertion portion is assumed to be a z axis (a positive direction and a negative direction are assumed to be an object side and an image side, respectively), and axes in two directions perpendicular to the z axis are assumed to be an x axis and a y axis, the 5D sensor 11 measures xyz coordinates (three-dimensional translational degree of freedom) of a distal end portion of the endoscope 2 and rotation angles around the x axis and the y axis (two rotational degrees of freedom) and outputs the xyz coordinates and the rotation angles as 5-degree-of-freedom information that includes three-dimensional translational-degree-of-freedom information about an image pickup position when a subject image is picked up, and information about each of the rotational degrees of freedom around the two axes orthogonal to the image pickup direction. Note that, according to such settings, the positive direction of the z axis is the image pickup direction, and the z axis passes through a center of an image pickup surface (therefore, an endoscopic image) of an image pickup device (that is, it is possible to determine an image pickup direction of a subject image based on the 5-degree-of-freedom information).

The endoscope 2 as described above is adapted to be connected to the video processor 3 and controlled.

The video processor 3 is provided with a signal processing portion 12, a control portion 13 and a light source portion 14.

The signal processing portion 12 performs signal processing of an image pickup signal outputted from the image pickup device of the endoscope 2 to generate endoscopic image data as a two-dimensional subject image.

The control portion 13 performs image pickup control of the endoscope 2 according to a user operation, transmits a drive signal to the image pickup device of the endoscope 2 to cause the image pickup device to pick up an image of an inside of a subject and generate an image pickup signal. Furthermore, the control portion 13 performs control to adjust an amount of illumination light of the light source portion 14 and switch on/off of light emission. The control portion 13 receives the 5-degree-of-freedom information from the endoscope 2 and transmits the 5-degree-of-freedom information to the image processing apparatus 5.

The light source portion 14 includes a light source configured to emit illumination light and radiates the illumination light to a proximal end side of the optical fibers of the endoscope 2. The illumination light is transmitted through the optical fibers and radiated to a subject from the distal end portion of the endoscope 2.

Here, in the present embodiment, a tubular structure such as a lumen is assumed as a subject, and luminal organs such as an intestine, a ureter, a renal pelvis, a renal calyx, and bronchus, or a pipe, a duct and the like are given as examples.

The video processor 3 is connected to the image processing apparatus 5 via a cable 4 that is, for example, a USB cable.

The cable 4 is adapted to transmit endoscopic image data and 5-degree-of-freedom information from the video processor 3 to the image processing apparatus 5 and transmit a control signal from the image processing apparatus 5 to the video processor 3, and it is a bi-directionally communicable communication line.

The image processing apparatus 5 includes an input/output interface (I/F) 15, a storage portion 16 and a control portion 17. The image processing apparatus 5 may be configured to have a personal computer execute a processing program, but may be configured as a dedicated processing apparatus.

The input/output interface (I/F) 15 is for the image processing apparatus 5 to perform data transmission/reception with external equipment, and is connected to the video processor 3, the monitor 6, the keyboard 7 and the mouse 8. The image processing apparatus 5 receives endoscopic image data and 5-degree-of-freedom information from the video processor 3 via the input/output I/F 15, transmits a control signal to the video processor 3, outputs a three-dimensional shape image generated from the endoscopic image data to the monitor 6, and receives signals generated from the keyboard 7 and the mouse 8 by user operations.

The storage portion 16 stores a processing program to be executed by the image processing apparatus 5, temporarily stores image data that is in image-process and nonvolatilely stores a three-dimensional shape image generated by the image processing. For example, the storage portion 16 is configured including various kinds of storage devices such as a hard disk, a RAM and a ROM.

The control portion 17 controls the image processing system 1 including the image processing apparatus 5 according to the processing program. Further, the control portion 17 executes image processing according to the processing program and generates a three-dimensional shape image from received endoscopic image data.

The monitor 6 is a display device configured to display the three-dimensional shape image generated by the image processing apparatus 5 and display a variety of information related to the image processing system 1.

The keyboard 7 and the mouse 8 are operation portions and are inputting portions 29 to be described later (see FIG. 2). The keyboard 7 and the mouse 8 output signals corresponding to user operations to the image processing apparatus 5. The control portion 17 performs control according to the processing program in response to signals inputted from the keyboard 7 and the mouse 8.

Next, functional blocks in the image processing apparatus 5 configured as described above will be described with reference to FIG. 2. FIG. 2 is a block diagram showing the configuration of the image processing apparatus 5.

The image processing apparatus 5 is provided with an image inputting portion 21, a three-dimensional image constructing portion 22, a positional relationship calculating portion 23, a three-dimensional shape image generating portion 24 and a storage portion 25. Here, the image inputting portion 21 substantially corresponds to the input/output I/F 15 described above. The storage portion 25 is substantially corresponds to the storage portion 16 described above. The three-dimensional image constructing portion 22, the positional relationship calculating portion 23 and the three-dimensional shape image generating portion 24 substantially correspond to the control portion 17 described above.

A two-dimensional subject image obtained by picking up an image of an inside of a subject is inputted to the image inputting portion 21. Three-dimensional translational-degree-of-freedom information about an image pickup position and 5-degree-of-freedom information including information about rotational-degree-of-freedom around each of two axes orthogonal to an image pickup direction are inputted as image pickup position information when the subject image is picked up.

The three-dimensional image constructing portion 22 constructs three-dimensional image data, which is a curved surface in three dimensions, based on the subject image. The three-dimensional image data constructed here becomes a comparison-source partial shape as described later.

The positional relationship calculating portion 23 arranges at least two different pieces of three-dimensional image data constructed by the three-dimensional image constructing portion 22 based on at least two different subject images, at predetermined positions based on image pickup position information described above, and calculates a positional relationship between the two different pieces of three-dimensional image data. More specifically, for the at least two different pieces of three-dimensional image data arranged at the predetermined positions, the positional relationship calculating portion 23 calculates a positional relationship showing a deviation around a rotation axis, between the two different pieces of three-dimensional image data, with an image pickup direction of the subject images determined based on the image pickup position information as a rotation axis, for example, with an image pickup direction of the subject images determined based on 5-degree-of-freedom information (the z axis described above) as a rotation axis.

Based on the positional relationship calculated by the positional relationship calculating portion 23, the three-dimensional shape image generating portion 24 generates a three-dimensional shape image by arranging the different pieces of three-dimensional image data in three-dimensional space such that the deviation between the different pieces of three-dimensional image data is corrected. More specifically, based on the positional relationship calculated by the positional relationship calculating portion 23, the three-dimensional shape image generating portion 24 generates a three-dimensional shape image obtained by rotating at least one of the two pieces of three-dimensional image data around the rotation axis so that the deviation around the rotation axis between the two different pieces of three-dimensional image data is minimized, to arrange the piece of three-dimensional image data in the three-dimensional space. By sequentially performing such a process for every two pieces of three-dimensional image data among a plurality of different pieces of three-dimensional image data, the three-dimensional shape image generating portion 24 can perform the process even when three or more pieces of three-dimensional image data exist (that is, for at least two different pieces of three-dimensional image data).

The storage portion 25 stores various information as described above about the storage portion 16. The storage portion 25 especially stores the three-dimensional shape image generated by the three-dimensional shape image generating portion 24. The three-dimensional shape image stored in the storage portion 25 becomes a comparison-destination partial shape as described later, and is compared relative to a comparison-source partial shape newly constructed by the three-dimensional image constructing portion 22, by the positional relationship calculating portion 23 to calculate a positional relationship.

Note that the storage portion 25 may store, for each partial shape, the partial shape together with a positional relationship with another partial shape (that is, the storage portion 25 may individually store each of a plurality of partial shapes). Or the storage portion 25 may store an overall partial shape configured by aligning a plurality of partial shapes based on positional relationships, or may store both.

The positional relationship calculating portion 23 described above includes a peripheral image generating portion 26, a characteristic part detecting portion 27 and a similarity degree calculating portion 28.

The peripheral image generating portion 26 generates two peripheral images of an inside of a subject by two-dimensionally developing two different pieces of three-dimensional image data, respectively.

For one of the two different pieces of three-dimensional image data (for example, peripheral images obtained by developing curved surfaces of the pieces of three-dimensional image data), the characteristic part detecting portion 27 detects a characteristic part based on a predetermined parameter. More specifically, for one of the two different pieces of three-dimensional image data, the characteristic part detecting portion 27 detects, for example, such a part where an amount of change in a luminance value is equal to or larger than a second threshold as the characteristic part.

The similarity degree calculating portion 28 divides the other of the two different pieces of three-dimensional image data into a plurality of areas and calculates a degree of similarity between each of the areas and the characteristic part detected by the characteristic part detecting portion 27.

Then, the positional relationship calculating portion 23 calculates a positional relationship when the similarity degree calculated by the similarity degree calculating portion 28 is equal to or higher than a predetermined threshold.

Next, the operation of the image processing system as described above will be described in more detail. First, FIG. 3 is a flowchart showing the operation of the image processing apparatus 5.

Figure 3:
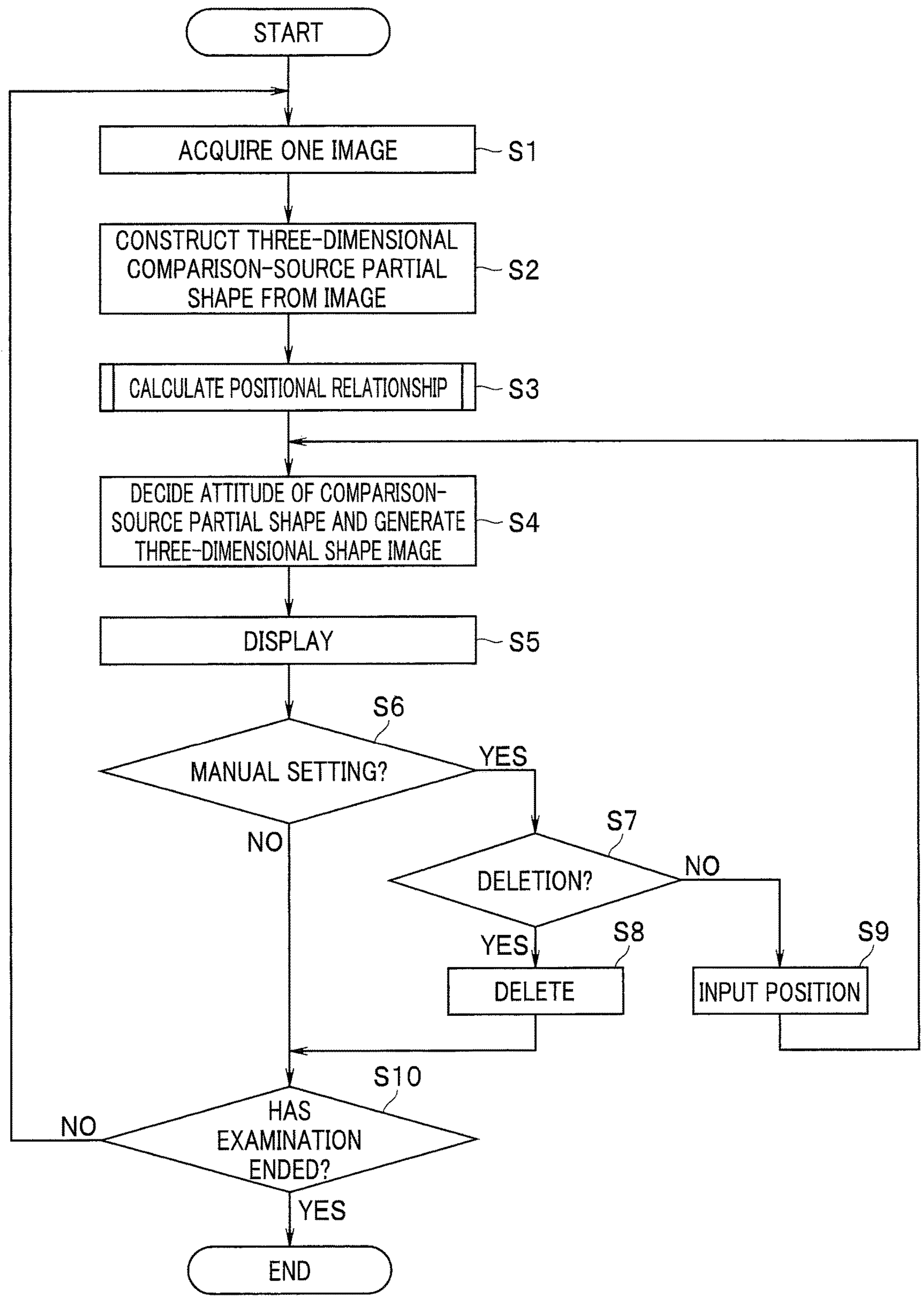
FIG. 3 is a flowchart showing operation of the image processing apparatus of the first embodiment.

A process shown in FIG. 3 is performed inside a subject such as luminal organ while the endoscope 2 is moved as necessary, and images of a plurality of time-series frames are acquired.

Figure 5:
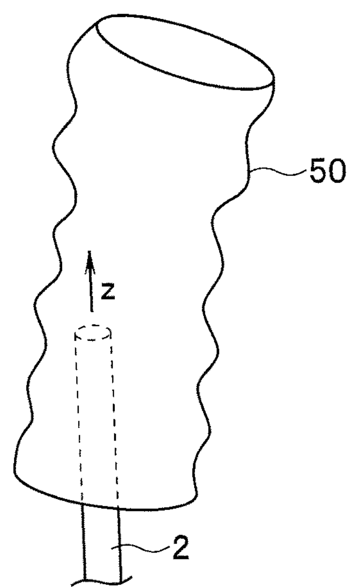
FIG. 5 is a diagram showing a state where an endoscope is inserted in a tubular subject in the first embodiment.

Here, FIG. 5 is a diagram showing a state where the endoscope 2 is inserted in a tubular subject 50. In the example shown in FIG. 5, the image pickup direction (the z axis direction) and a depth direction of the tubular subject 50 deviate from each other.

Note that the image processing apparatus 5 is not limited to acquiring endoscopic image data from the endoscope 2 as shown in FIG. 1 in real time but may acquire endoscopic image data via a recording device such as a recording medium, or may acquire endoscopic image data via a communication line such as a network. Therefore, it is also possible to sequentially acquire images already picked up by the endoscope 2 and recorded in a recording device such as a hard disk, from the recording device and execute the process shown in FIG. 3.

When the process is started, the image inputting portion 21 acquires an image corresponding to one frame from the video processor 3 (step S1). Though one frame of a movie picked up and acquired in time series (or still images consecutively picked up in time series) is acquired here, the acquisition is not limited to acquiring all of a plurality of frames constituting the movie. For example, one frame for every ten frames may be acquired.

Figure 6:
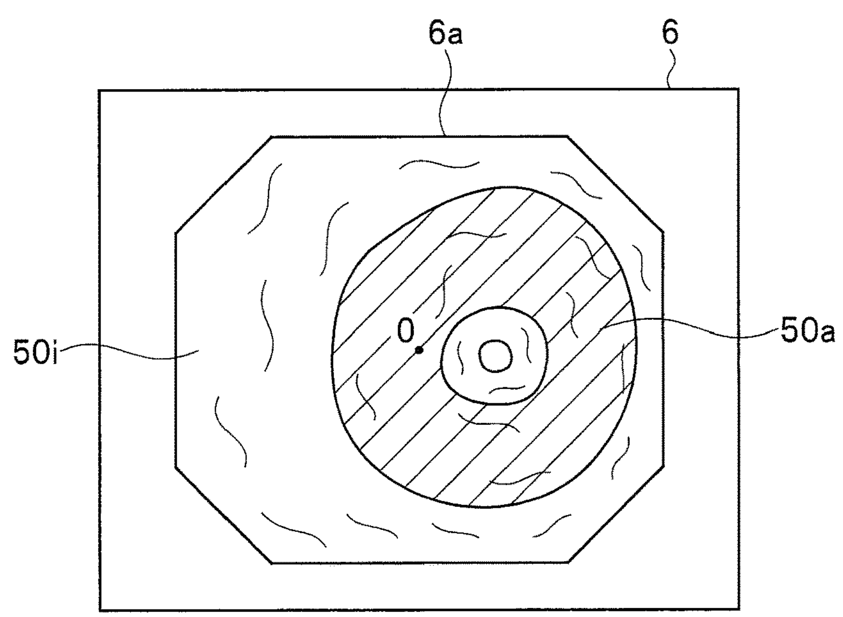
FIG. 6 is a diagram showing a state of setting an image area for constructing three-dimensional image data in an endoscopic image in the first embodiment.

FIG. 6 is a diagram showing a state where an image area for constructing three-dimensional image data is set in an endoscopic image 6*a*. When an image corresponding to one frame acquired by the image inputting portion 21 is displayed on the monitor 6, for example, the image is as shown in FIG. 6. Here, O in FIG. 6 indicates a center of the endoscopic image 6*a*, and it can be thought that the z axis is set in a perpendicular direction passing through the center O.

In the endoscopic image 6*a* displayed on the monitor 6, a subject image 50*i* of a subject 50 is shown. At this time, in the state shown in FIG. 5, since the z axis direction and the depth direction of the subject 50 deviate from each other as described above, a deep part of the subject 50 is deviated from the center O in the endoscopic image 6*a* too.

Next, the three-dimensional image constructing portion 22 constructs a three-dimensional comparison-source partial shape from the one two-dimensional subject image acquired by the image inputting portion 21 (step S2). That is, the three-dimensional image constructing portion 22 constructs three-dimensional image data, which is a curved surface in three dimensions, based on an image area 50*a* (see FIG. 6) in the endoscopic image 6*a*, in which a subject part existing in a certain distance range from the objective lens of the endoscope 2.

Here, a method for the three-dimensional image constructing portion 22 to construct the three-dimensional image data, which is a curved surface in three dimensions, based on the one two-dimensional subject image, does not depend on a particular method. Various methods can be widely adopted. For example, it can be assumed that, since illumination light is radiated to perform observation in a lumen, which is a dark part, a pixel with a low luminance exists in the distance, and a pixel with a high luminance exists in the near distance. Based on the assumption, a three-dimensional shape can be estimated and constructed. A method of estimating a shape of a target from an image corresponding to one frame like the shape-from-shading method is also known. The method is not limited to the above methods, but any other arbitrary method can be adopted.

Figure 7:
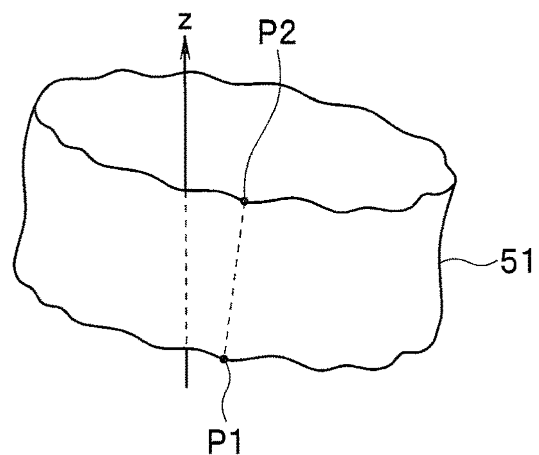
FIG. 7 is a diagram showing an example of the three-dimensional image data constructed from the endoscopic image in the first embodiment.

When a subject is a tubular structure as described above, a constructed comparison-source partial shape 51 has a tubular curved surface similar to a surface of the original tubular structure (though the length is shorter) as shown in FIG. 7. Here, FIG. 7 is a diagram showing an example of the three-dimensional image data constructed from the endoscopic image 6*a*.

Note that when the subject 50 has a branch (see FIG. 8), for example, a process is performed as follows. Here, FIG. 8 is a diagram showing an example when the comparison-source partial shape 51 constructed once is a branched tubular shape.

Figure 8:
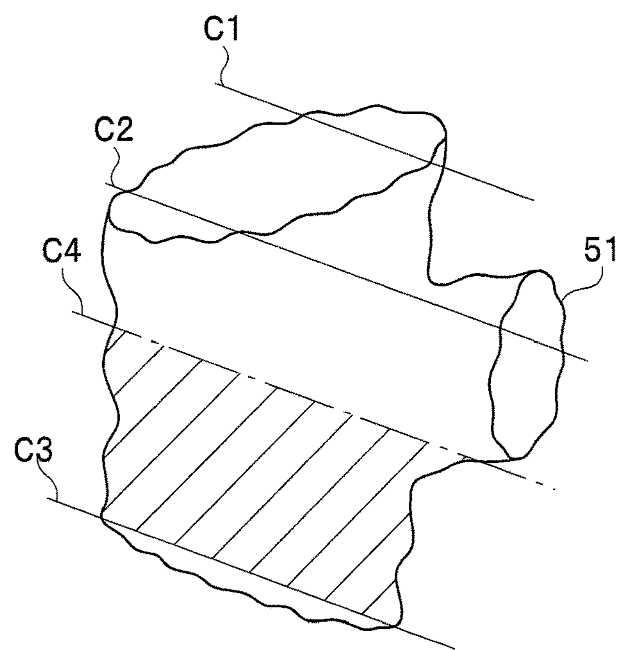
FIG. 8 is a diagram showing an example when a comparison-source partial shape constructed once is in a branched tubular shape in the first embodiment.

If the comparison-source partial shape 51 is in the shape as shown in FIG. 8, a plane fitted to (optimized for) an edge of the comparison-source partial shape 51 once constructed, where the edge is on a side nearer to the endoscope 2, (i.e., a plane most similar to the edge nearer to the endoscope 2) is calculated first. It is assumed that the plane calculated here is a cross section C3 shown in FIG. 8.

Figure 9:
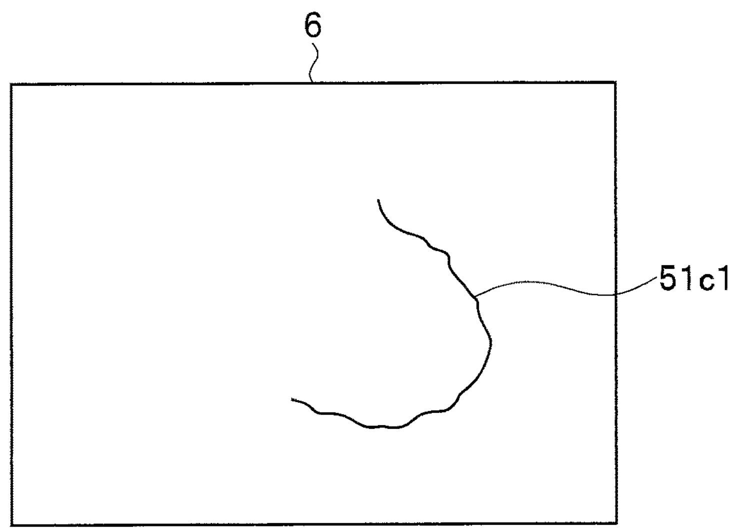
FIG. 9 is a diagram showing an example of a comparison-source partial shape on a cross section C1 in FIG. 8 in the first embodiment.
Figure 10:
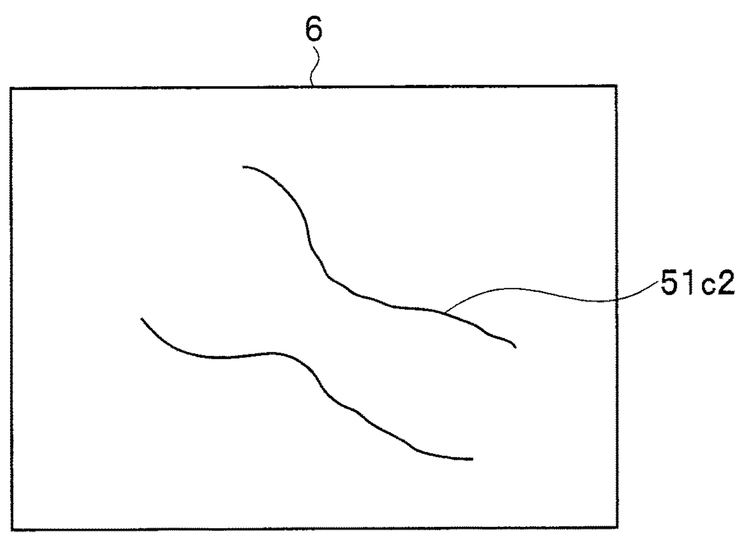
FIG. 10 is a diagram showing an example of a comparison-source partial shape on a cross section C2 in FIG. 8 in the first embodiment.
Figure 11:
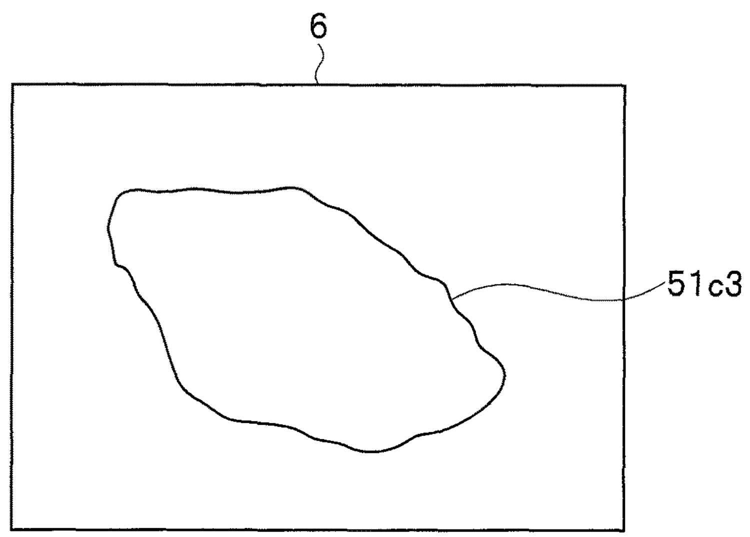
FIG. 11 is a diagram showing an example of a comparison-source partial shape on a cross section C3 in FIG. 8 in the first embodiment.

Examples of images when the comparison-source partial shape 51 is cut along the cross section C3 and some cross sections C1 and C2 in parallel to the cross section C3 are shown in FIGS. 9 to 11. Here, FIG. 9 is a diagram showing an example of a comparison-source partial shape on the cross section C1 in FIG. 8; FIG. 10 is a diagram showing an example of a comparison-source partial shape on the cross section C2 in FIG. 8; and FIG. 11 is a diagram showing an example of a comparison-source partial shape on the cross section C3 in FIG. 8.

As shown in the figures, a cross-sectional shape 51*c*1 of the comparison-source partial shape 51 forms an open curve when the comparison-source partial shape 51 is cut along the cross section C1; a cross-sectional shape 51*c*2 of the comparison-source partial shape 51 forms a plurality of open curves when the comparison-source partial shape 51 is cut along the cross section C2; and a cross-sectional shape 51*c*3 of the comparison-source partial shape 51 forms a closed curve when the comparison-source partial shape 51 is cut along the cross section C3.

In such a case, a cross section C4 that satisfies conditions (1) and (2) as shown below is searched for while a cross section for search is gradually translated from the cross section C3 toward the cross section C1 side.

(1) When the cross section for search is translated from the cross section C3, the cross section C4 is reached while the state where the cross-sectional shape of the comparison-source partial shape 51 on the cross section for search is a closed curve is maintained.

(2) An interplanar distance between the cross section C4 and the cross section C3 is equal to or longer than a predetermined threshold.

Then, a part of the comparison-source partial shape 51 between the cross section C3 and the cross section C4 that satisfies the conditions (1) and (2) is set as a final comparison-source partial shape 51 (see a hatched part in FIG. 8).

It is assured by the condition (1) that the final comparison-source partial shape 51 forms a single tubular shape (without a branch), and a length of the final comparison-source partial shape 51 in a duct direction equal to or longer than a predetermined threshold can be secured by the condition (2).

Figure 4:
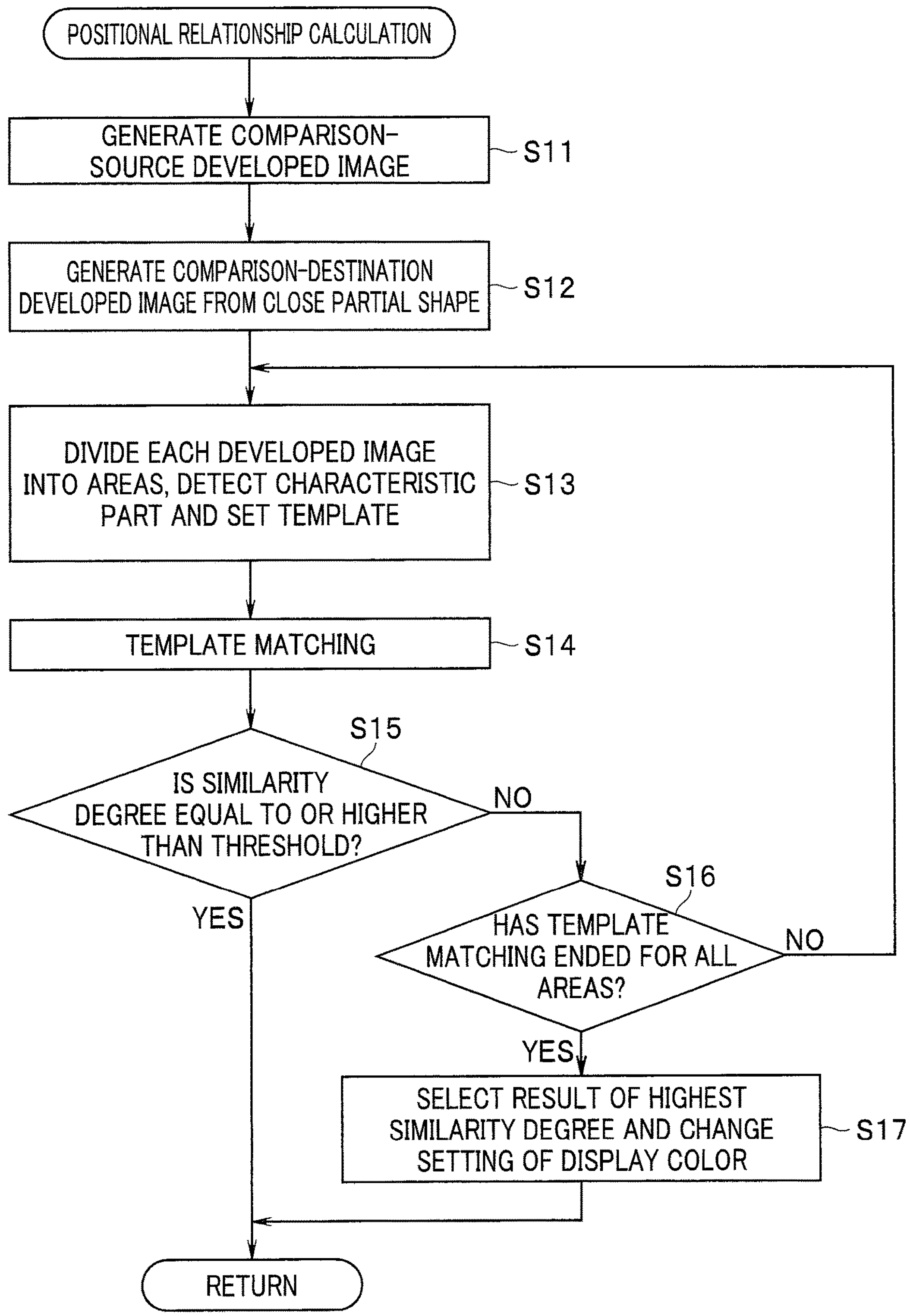
FIG. 4 is a flowchart showing a positional relationship calculating process in the image processing apparatus of the first embodiment.

Then, the positional relationship calculating portion 23 calculates a positional relationship between the comparison-source partial shape constructed by step S2 and a comparison-destination partial shape constructed by the three-dimensional image constructing portion 22 in the past and stored in the storage portion 25 as shown in FIG. 4 (step S3).

Here, FIG. 4 is a flowchart showing a positional relationship calculating process in the image processing apparatus 5.

When entering the process, the peripheral image generating portion 26 sets one point P1 at an arbitrary position on an edge in the negative direction of the z axis (on a side nearer to the endoscope 2), for the comparison-source partial shape 51 in a short tubular shape calculated at step S2 as shown in FIG. 7. Furthermore, the peripheral image generating portion 26 calculates a point P2 nearest to the point P1 on an edge in the positive direction of the z axis (on a side farther from the endoscope 2).

Figure 12:
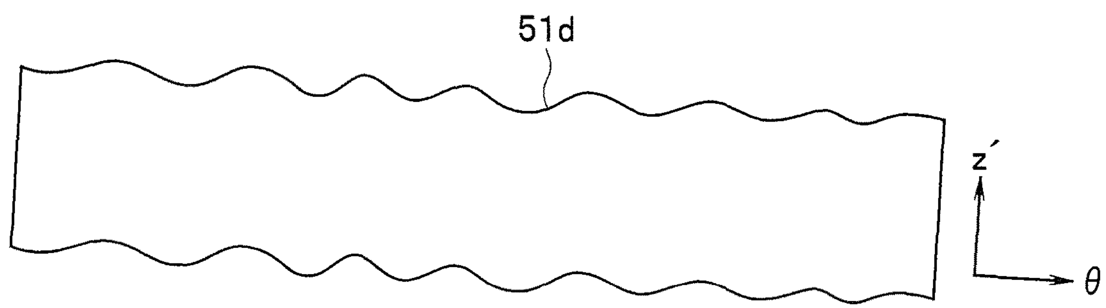
FIG. 12 is a diagram showing an example in which the three-dimensional image data constructed from the endoscopic image is developed in two dimensions in the first embodiment.

Then, the peripheral image generating portion 26 cuts the comparison-source partial shape 51 along a line segment P1P2 connecting the point P1 and the point P2 and develops the comparison-source partial shape into a plane to generate a developed image 51*d* as shown in FIG. 12. FIG. 12 is a diagram showing an example of developing the three-dimensional image data constructed from the endoscopic image 6*a* into two dimensions. In FIG. 12, a horizontal axis is a θ axis showing, for example, by an angle, a circumferential direction position of the comparison-source partial shape 51 forming a short tubular shape, around the z axis and a vertical axis is a z' axis that almost corresponds to the z axis and shows whether near to or far from the endoscope 2.

At the time of constructing the comparison-source partial shape 51, which is three-dimensional image data, from the endoscopic image 6*a*, what is generated varies depending on what algorithm is used. For example, monochrome three-dimensional image data of an uneven shape of the subject based on luminance values is generated in one case, and color three-dimensional image data, which is the endoscopic image 6*a* formed into an uneven shape and three-dimensionalized as the endoscopic image 6*a* is, is generated in another.

Figure 13:
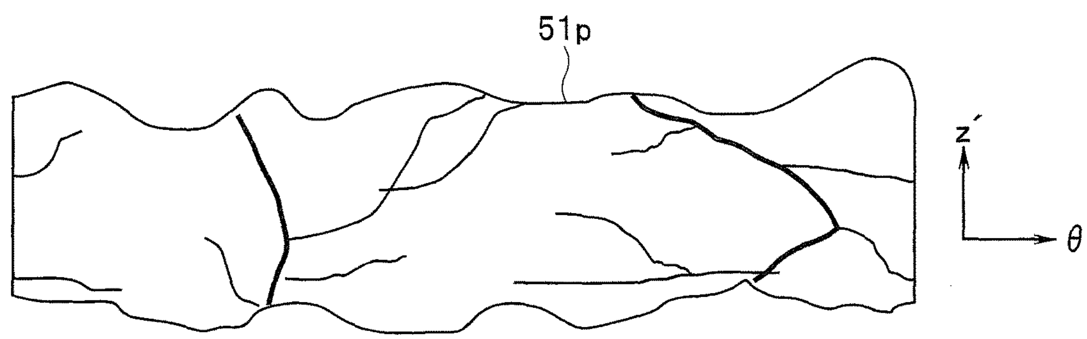
FIG. 13 is a diagram showing an example of a peripheral image obtained by attaching an endoscopic image to the developed image in the first embodiment.

At this time, in the latter case, the generated developed image 51*d* becomes a comparison-source developed image 51*p*, which is a peripheral image (an image for matching to be used for template matching described later), as the generated developed image 51*d* is. On the other hand, in the former case, the peripheral image generating portion 26 generates the comparison-source developed image 51*p* by attaching the endoscopic image 6*a* to the developed image 51*d* as texture. FIG. 13 is a diagram showing an example of the peripheral image obtained by attaching the endoscopic image 6*a* to the developed image 51*d*.

At the time of generating the peripheral image, even if the comparison-source partial shape 51 is merely cut along the line segment P1P2 and developed, the uneven shape remains, and a complete plane is not obtained. Therefore, for example, the developed image is parallel-projected to a plane in parallel to the developed image, after cutting and developing the comparison-source partial shape 51, to generate a final peripheral image.

In this way, the peripheral image generating portion 26 generates the comparison-source developed image 51*p*, which is a peripheral image, from the comparison-source partial shape 51 (step S11).

Further, the peripheral image generating portion 26 reads out a partial shape close to the comparison-source partial shape 51 from among one or more three-dimensional shape images stored in the storage portion 25, sets the partial shape as a comparison-destination partial shape and generates a comparison-destination developed image similarly to the above (step S12).

Figure 14:
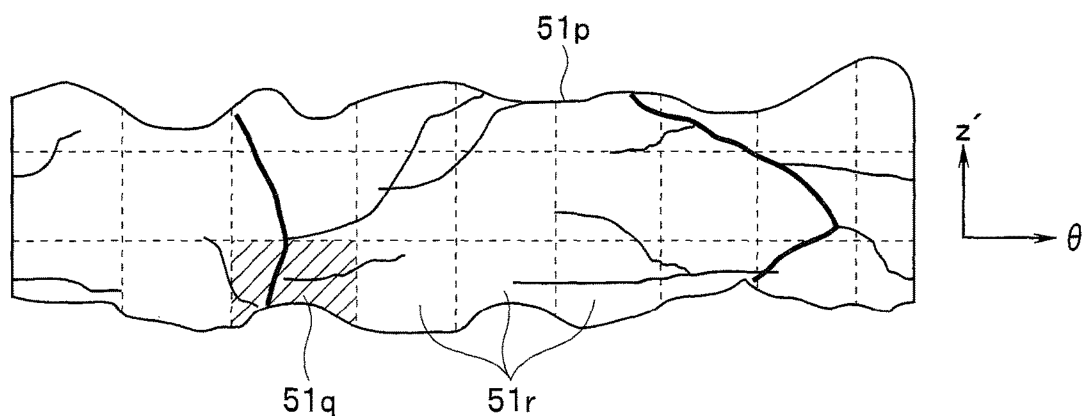
FIG. 14 is a diagram showing an example of dividing the peripheral image into a plurality of areas and setting a template as a characteristic part in the first embodiment.

Next, the characteristic part detecting portion 27 divides one of the comparison-source developed image 51*p* and a comparison-destination developed image 51*p*', for example, the comparison-source developed image 51*p* into a plurality of areas 51*r* as shown in FIG. 14, calculates a luminance change amount of each area 51*r*, and sets an area 51*r*, the luminance change amount of which is larger than the second threshold (preferably, the largest), as a template image 51*q* (step S13).

More specifically, as the luminance change amount, an example of using distribution (an example of a predetermined parameter) of luminance values (or values corresponding to luminance such as G components) of respective pixels in each area 51*r* is given. In this case, the larger the distribution is, the larger the luminance change amount is. As another example, edges are extracted using Canny method or the like, and the number of pixels judged to be an edge in each area 51*r* may be used as an evaluation value of the luminance change amount. In this case, the more pixels are judged to be edges, the larger the luminance change amount is.

Note that, in a case where a subject is, for example, a body cavity of a living body having blood vessels, it is thought that a part with a lot of blood vessels is suitable to be set as a template because texture is clear. It is thought that an R component among RGB color components is large in a blood vessel part, and G/R, a ratio of G, which is a component corresponding to luminance, to R is relatively a small value. Therefore, G/R is used as an index value to calculate an index value G/R for each pixel, and, for each area 51*r*, the number of pixels the index value G/R of which is smaller than a predetermined threshold is counted. Then, an area 51*r* for which the number of counted pixels is largest may be set as the template image 51*q*.

Since it is desirable to select the template image 51*q* from areas 51*r* on a side close to the comparison-destination developed image 51*p*', more specifically, on the endoscope 2 side (the negative direction side of the z' axis) here, weighting may be performed in order to make it easy for the areas 51*r* on the endoscope 2 side to be selected at the time of searching for and evaluating an area 51*r* suitable as the template image 51*q*. As a specific example of a weight, for example, an evaluation value of each area 51*r* on a first line from the endoscope 2 side is multiplied by a weight k; an evaluation value of each area 51*r* on a second line is multiplied by a weight k/2; and an evaluation value of each area 51*r* on a third line is multiplied by a weight k/4. By setting the weight k as described above, it is possible to prevent wrong matching from being performed when an area similar to the template image 51*q* exists in areas other than areas on an edge side where matching with the template image 51*q* is highly possible (the respective areas 51*r* on the first line).

The weight is not limited to the above example. The value of the weight k may be set according to a moving speed of the endoscope 2 in the subject or a size of the developed image 51*d*.

Alternatively, a process shown as below may be performed. That is, selection of the template image 51*q* is performed with only the respective areas 51*r* on the first line from the endoscope 2 side as an evaluation target. Then, when the flow returns to the process of step S13 again after the steps S15 and S16 because a result of "template matching" of step S14 described later is not favorable, selection of the template image 51*q* is performed with the respective areas 51*r* on the second line from the endoscope 2 side as an evaluation target. Similarly, the third and subsequent lines are sequentially processed as an evaluation target.

Then, the similarity degree calculating portion 28 divides the comparison-destination developed image 51*p*' into a plurality of areas 51*r*' and performs template matching for the comparison-destination developed image 51*p*' using the template image 51*q* obtained at step S13 (step S14). As an example of a specific template matching method, square of a difference for each pixel, between the template image 51*q* and each of the areas 51*r*' of the comparison-destination developed image 51*p*', is determined, and a sum total of squares of the differences for the pixels is calculated, and, for example, a reciprocal of the sum total can be set as a similarity degree. Such template matching corresponds to calculation of a similarity degree of texture. If the template image 51*q* and an area 51*r*' are similar, the sum total of squares of differences is small, and the similarity degree is high. Note that the template matching method is not limited to the above, but various methods can be widely applied.

Then, it is judged whether or not the highest similarity degree obtained as a result of template matching is equal to or higher than a predetermined threshold (step S15). Note that if an area 51*r*' with a similarity degree equal to or higher than the predetermined threshold is found while template matching is being performed, a process of stopping performing further template matching and setting the found area 51*r*' as a result of template matching may be performed.

Figure 15:
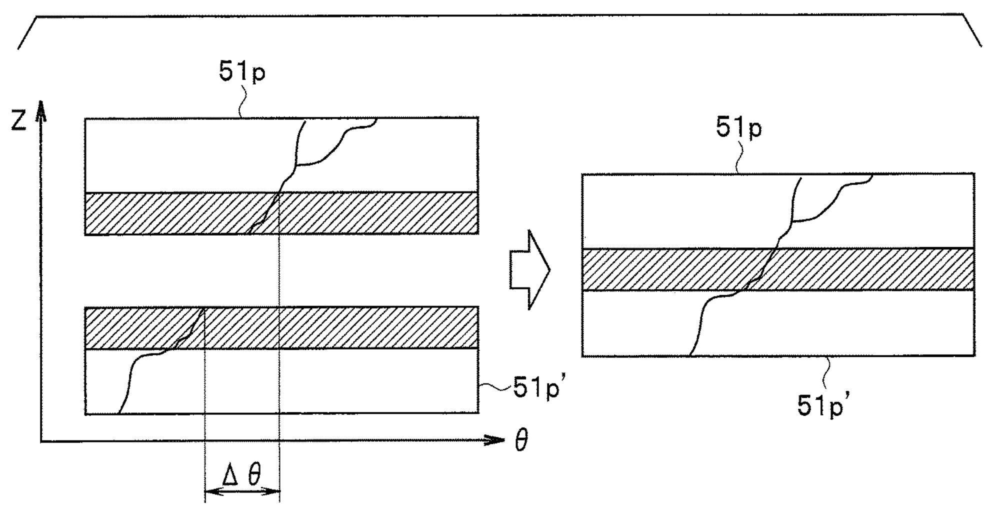
FIG. 15 is a conceptual diagram showing a state of overlapping a comparison-source developed image and a comparison-destination developed image so as to eliminate a positional deviation angle $\Delta\theta$ in the first embodiment.

If the highest similarity degree is equal to or higher than the predetermined threshold, a positional relationship between the comparison-source developed image 51*p* and the comparison-destination developed image 51*p*' when the similarity degree equal to or higher than the threshold is obtained, more specifically, a positional deviation angle $\Delta\theta$ around the z axis is a result of the positional relationship calculating process shown in FIG. 4. A conceptual diagram of a developed image obtained by overlapping the comparison-source developed image 51*p* and the comparison-destination developed image 51*p*' such that the positional deviation angle $\Delta\theta$ by the positional relationship calculating process is eliminated is shown in FIG. 15. FIG. 15 is a conceptual diagram showing a state of overlapping the comparison-source developed image 51*p* and the comparison-destination developed image 51*p*' so as to eliminate the positional deviation angle $\Delta\theta$.

On the other hand, if the highest similarity degree is lower than the predetermined threshold, it is judged whether template matching for all of areas 51*r* suitable to be set as the template image 51*q* has been performed or not (step S16).

If an unset area 51$r$ still exists, the flow returns to step S13 to newly set the template image 51$q$ (therefore, such an area 51$r$ that is already set as the template image 51$q$ is not set again), and the process as described above is performed.

If it is judged at step S16 that template matching has been performed for all the areas 51$r$ suitable to be set as the template image 51$q$, it means that such an area 51$r'$ that a degree of similarity with the template image 51$q$ is equal to or higher than the threshold has not been found in the comparison-destination developed image 51$p'$ no matter what the template image 51$q$ is set.

In this case, a positional relationship between the comparison-source developed image 51$p$ and the comparison-destination developed image 51$p'$, more specifically, the positional deviation angle $\Delta\theta$ around the z axis when the highest similarity degree among all the calculated similarity degrees is obtained is selected, and a display color of the comparison-source partial shape 51, which is three-dimensional image data corresponding to the comparison-source developed image 51$p$, is changed to be a color different from the comparison-destination partial shape (step S17).

If the process of S17 has been performed or if it is judged at step S15 that the similarity degree is equal to or higher than the threshold, the flow returns to the process shown in FIG. 3 (step S4 described above).

Note that though an example of dividing the comparison-source developed image 51$p$ and the comparison-destination developed image 51$p'$ into predetermined areas and performing template matching for each of the areas has been shown here, the present embodiment is not limited to the method. More specifically, it is possible to, similarly to techniques of Japanese Patent Application Laid-Open Publication No. H07-262370 and the like, which is a well-known technique, divide only the comparison-source developed image 51$p$ into areas 51$r$, set the template image 51$q$ and perform template matching while displacing the template image 51$q$ for each predetermined pixel of the comparison-destination developed image 51$p'$. By adopting such a scheme, it becomes possible to perform highly accurate template matching even if pixels, the luminance change amount of which is large, are arranged on a boundary between areas 51$r'$, in comparison with dividing the comparison-destination developed image 51$p'$ into the respective areas 51$r'$ to perform template matching.

Returning to the process of FIG. 3, based on the positional relationship calculated by the positional relationship calculating process of step S3, more specifically, the positional deviation angle $\Delta\theta$ around the z axis of the comparison-source partial shape 51 relative to the comparison-destination partial shape, the three-dimensional shape image generating portion 24 generates a three-dimensional shape image obtained by rotating at least one of the comparison-source partial shape 51 and the comparison-destination partial shape, for example, the comparison-source partial shape 51 around the z axis to arrange the comparison-source partial shape 51 in three-dimensional space (step S4). Thereby, an attitude of the comparison-source partial shape 51 is decided, and the three-dimensional shape image is generated.

Note that though it is preferable that the comparison-source partial shape 51 is coupled with a comparison-destination partial shape 53 (see FIG. 16) in the generated three-dimensional shape image, it is sufficient if a mutual positional relationship is uniquely defined even when both are not coupled with each other. It does not matter if the comparison-source partial shape 51 and the comparison-destination partial shape 53 are merely arranged in one three-dimensional space (shape space) based on a decided positional relationship.

Then, the generated three-dimensional shape image is outputted to the monitor 6 and displayed (step S5). The generated three-dimensional shape image is also stored in the storage portion 25.

Figure 16:
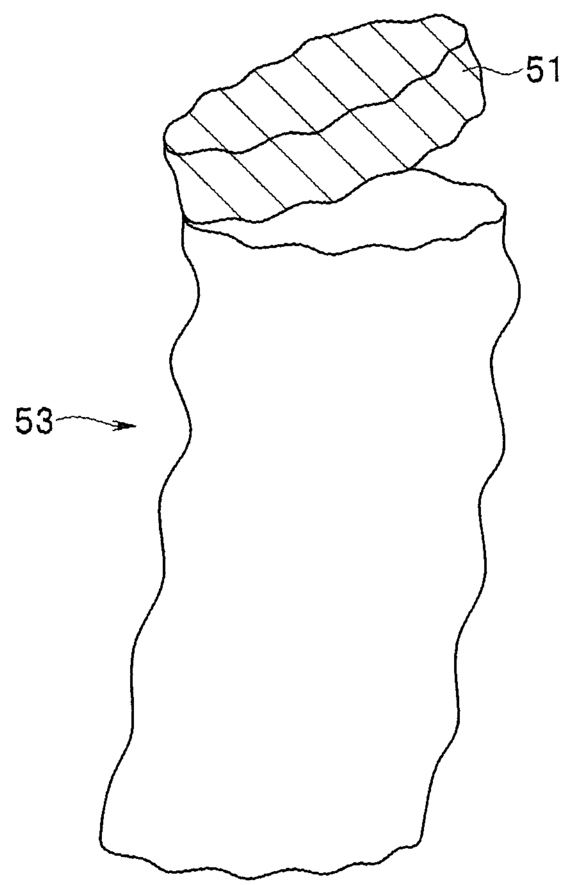
FIG. 16 is a diagram showing an example of displaying a comparison-source partial shape in a color different from a color of a comparison-destination partial shape when a similarity degree of template matching is low, in the first embodiment.

If the display color of the comparison-source partial shape 51 is changed at step S17 described above, the newly coupled comparison-source partial shape 51 is displayed in a different color relative to the comparison-destination partial shape 53 obtained by coupling the plurality of partial shapes in the past, as shown in FIG. 16. FIG. 16 is a diagram showing an example of displaying the comparison-source partial shape 51 in a color different from a color of the comparison-destination partial shape 53 when the similarity degree of template matching is low (that is, when it is possible that arrangement of the comparison-source partial shape 51, therefore, coupling between the comparison-source partial shape 51 and the comparison-destination partial shape is inappropriate).

Note that, though a user is informed of the low similarity degree by color here, the user's attention may also be called by an arbitrary method, for example, by changing a luminance, thickening (or thinning, or showing by a dotted line or the like) an outline, blinking display, making a notification by voice, or combination of the above.

After that, it is judged whether or not the user who has seen the display has performed manual setting from the inputting portion 29 (step S6).

If it is judged that the user has performed manual setting, it is further judged whether setting content is deletion or not (step S7).

Then, if it is judged that the content is deletion, the comparison-source partial shape 51, which is a partial shape generated last, is deleted (step S8). At this time, not only the displayed image but also the comparison-source partial shape 51 stored in the storage portion 25 is also deleted.

Therefore, the inputting portion 29 functions as a specifying portion configured to specify a partial shape to be a deletion target, and the image processing apparatus 5 functions as a deleting portion configured to delete the specified partial shape. At the time of the user specifying the deletion process, since the comparison-source partial shape 51 is displayed in a color different from the color of the comparison-destination partial shape 53 when the similarity degree is low as described above, the user's attention is called, and the user can easily judge whether or not to perform deletion.

If it is judged at step S7 that the setting content is not deletion, the position of the comparison-source partial shape 51 is to be manually adjusted. Therefore, a positional relationship of the comparison-source partial shape 51 relative to the comparison-destination partial shape 53 is set based on an input value (step S9). More specifically, according to a rotation angle inputted from the inputting portion 29, the three-dimensional shape image generating portion 24 that functions as a partial shape rotating portion causes the comparison-source partial shape 51, which is a partial shape generated last, to rotate.

When the process of step S9 has been performed, the flow returns to step S4, and a three-dimensional shape image is generated based on the inputted positional relationship.

If it is judged at step S6 that manual setting has not been performed, or if the deletion process of step S8 has been performed, it is judged whether the examination has ended or not (step S10).

If it is judged that the examination has not been ended, the flow returns to step S1, where an image corresponding to next one frame is acquired, and the process as described above is repeated.

On the other hand, if it is judged that the examination has ended, the process is ended.

Note that though the template image 51*q* is set based on the luminance change amounts of the areas 51*r*, and template matching is performed based on texture at steps S13 and S14 described above, this is not limitative. As a modification, alignment may be performed, for example, using hues (another example of the predetermined parameter).

In this case, in the process of step S13, after dividing the comparison-source developed image 51*p* into the plurality of areas 51*r*, an average value of hues of respective pixels constituting each of the areas 51*r* on the first line from the endoscope 2 side (the side nearer to the comparison-destination developed image 51*p*') is calculated.

Similarly, in the process of step S14, after dividing the comparison-destination developed image 51*p*' into the plurality of areas 51*r*, an average value of hues of respective pixels constituting each of the areas 51*r* on the first line from the side nearer to the comparison-source developed image 51*p* is calculated. Then, a positional relationship in which the hue of the comparison-source developed image 51*p* and the hue of the comparison-destination developed image 51*p*' match each other most is searched for while relative positions of the comparison-source developed image 51*p* and the comparison-destination developed image 51*p*' are changed.

More specifically, one arbitrary area 51*r* is selected from each of the first line of the comparison-source developed image 51*p* and the first line of the comparison-destination developed image 51*p*', an area number 1 is given to each arbitrary area 51*r*, and a hue difference Hue (1, 1) is calculated. Similarly, one area 51*r* adjoining each selected area 51*r* in the same θ direction is selected, an area number 2 is given to each adjoining area 51*r*, and a hue difference Hue (2, 2) is calculated. Furthermore, hue differences Hue (3, 3) to Hue (n, n) are similarly calculated (here, n is the number of areas 51*r* existing on one line). Then, for example, a sum of squares, Σ[{Hue (i, i)}^2] (i=1 to n) of all the differences is calculated (or, a sum of absolute differences or the like may be calculated). Here, it is assumed that a symbol "^2" indicates square. A reciprocal of the sum of squares calculated in this way can be the similarity degree.

A similarity degree that is highest (corresponding to a sum of squares that is smallest) is regarded as the similarity degree obtained at step S14, and the process of step S15 is performed.

If it is judged at step S15 that the similarity degree is lower than the threshold, and it is judged at step S16 that a combination of different lines for which template matching has not been performed between the comparison-source developed image 51*p* and the comparison-destination developed image 51*p*' exists, the flow returns to step S13, and template matching can be sequentially performed for combinations of different lines between the comparison-source developed image 51*p* and the comparison-destination developed image 51*p*', for example, the first line and the second line, the second line and the first line, the second line and the second line, and the like.

Template matching based on texture makes it possible to accurately align positions of partial shapes, but it is on an assumption that the partial shapes overlap with each other. In comparison, according to the modification using hues, an advantage exists that it is possible to perform alignment even when a gap exists between partial shapes.

According to the first embodiment as described above, for at least two different pieces of three-dimensional image data constructed based on at least two different subject images, a positional relationship between the respective pieces of three-dimensional image data is calculated, and a three-dimensional shape image is generated by arranging the different pieces of three-dimensional image data in three-dimensional space based on the positional relationship. Therefore, it is possible to generate a more accurate three-dimensional shape image without information about a rotational degree of freedom around an image pickup direction.

Further, the three-dimensional shape image is generated such that a deviation between the two different pieces of three-dimensional image data around the rotation axis is minimized, with an image pickup direction determined based on 5-degree-of-freedom information as a rotation axis. Therefore, it is possible to easily decide the rotation axis and accurately generate the three-dimensional shape image.

Furthermore, a characteristic part is detected from one of the pieces of three-dimensional image data based on a predetermined parameter, and the other is divided into a plurality of areas to calculate a degree of similarity with the characteristic part. Then, a positional relationship when the similarity degree is equal to or higher than a predetermined threshold is calculated. Therefore, it is possible to appropriately perform template matching based on the characteristic part.

Three-dimensional image data is developed into two dimensions to generate a peripheral image, and the characteristic part is detected from the peripheral image to perform template matching. Therefore, it is possible to handle a plane instead of handling a curved surface in the three-dimensional space, and it becomes possible to significantly reduce an operation load.

In addition, since a part where an amount of luminance value change is equal to or larger than the second threshold is detected as the characteristic part, it is possible to detect the characteristic part in both of a case of color three-dimensional image data and a case of monochrome three-dimensional image data.

In the case of setting an area 51*r* that the number of pixels the index value G/R of which is smaller than a predetermined threshold is the largest as the template image 51*q*, an area with a lot of blood vessels in a body cavity of a living body can be appropriately set as the template image 51*q*.

Even if it is judged at step S15 in FIG. 4 that the similarity degree is equal to or higher than the threshold, template matching may be performed for all the areas 51*r*. At that time, by temporarily storing the area 51*r*, the similarity degree of which is judged to be equal to or higher than the threshold, and, after template matching for all the areas 51*r* ends, selecting a positional relationship between the comparison-source developed image 51*p* and the comparison-destination developed image 51*p*' when the highest similarity degree among all calculated similarity degrees is obtained, it becomes possible to obtain a more accurate matching result.

[Second Embodimen]

Figure 17:
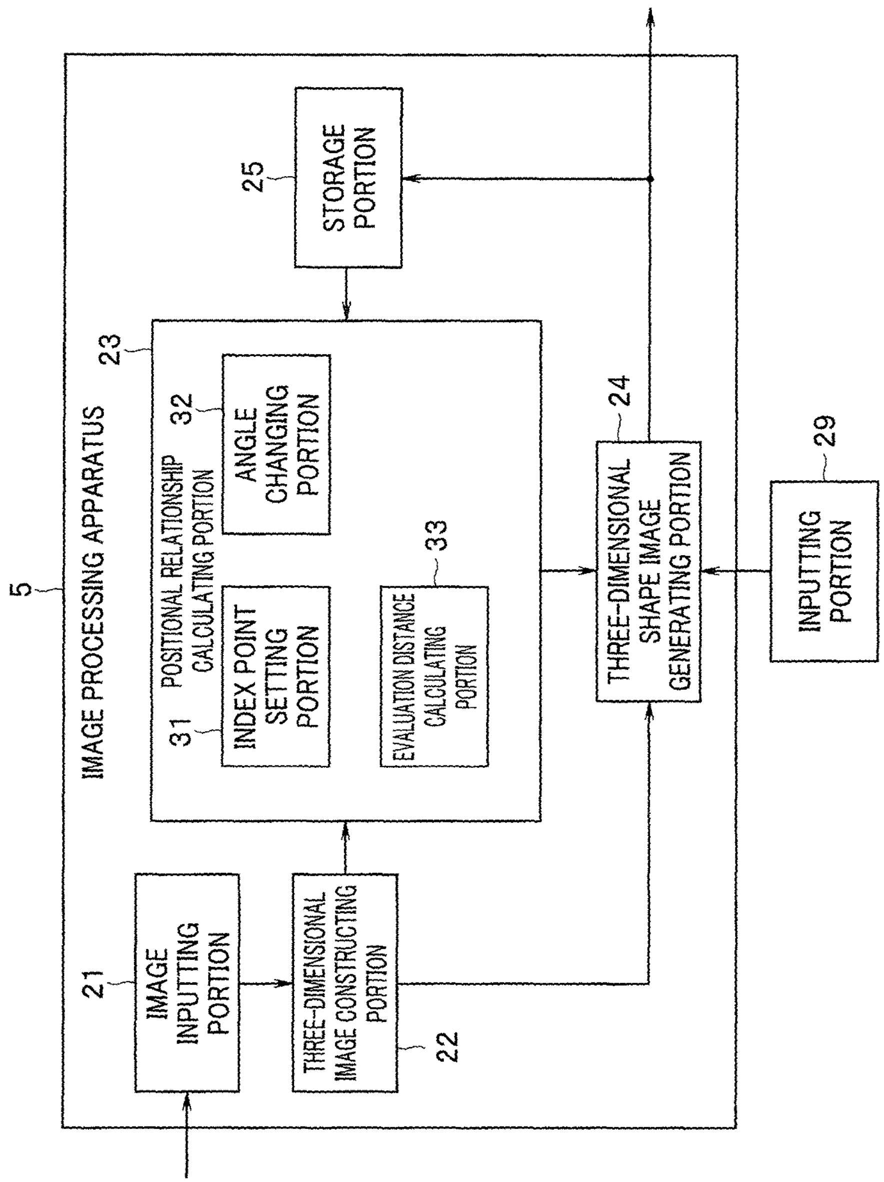
FIG. 17 is a block diagram showing a configuration of an image processing apparatus of a second embodiment of the present invention.

FIGS. 17 to 20 show a second embodiment of the present invention, and FIG. 17 is a block diagram showing a configuration of an image processing apparatus 5.

In the second embodiment, as for portions similar to portions in the first embodiment described above, the same reference numerals will be given, and description will be appropriately omitted. Description will be made mainly on different points.

In the first embodiment described above, a positional relationship between the comparison-source partial shape 51 and the comparison-destination partial shape is calculated so that textures, hues or the like of images match. In the present embodiment, however, a positional relationship is calculated so that facing edges 51*c* and 52*c* of the comparison-source partial shape 51 and a comparison-destination partial shape 52 may have continuity (to be smooth) as a shape.

Figure 2:
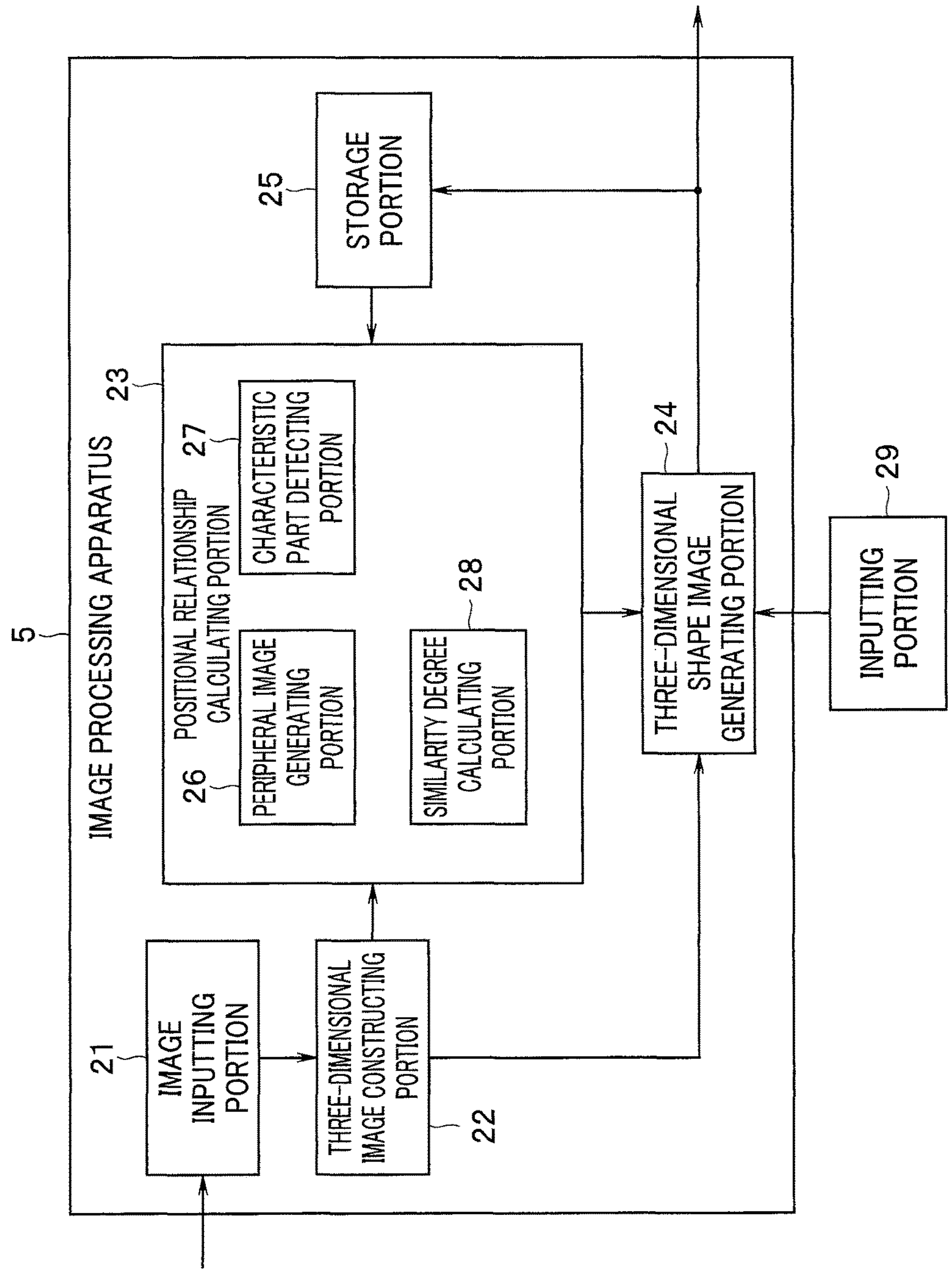
FIG. 2 is a block diagram showing a configuration of an image processing apparatus of the first embodiment.

In comparison with the image processing apparatus 5 shown in FIG. 2 of the first embodiment described above, the image processing apparatus 5 of the present embodiment is different in a configuration of the positional relationship calculating portion 23.

That is, the positional relationship calculating portion 23 of the present embodiment is provided with an index point setting portion 31, an angle changing portion 32 and an evaluation distance calculating portion 33.

Figure 19:
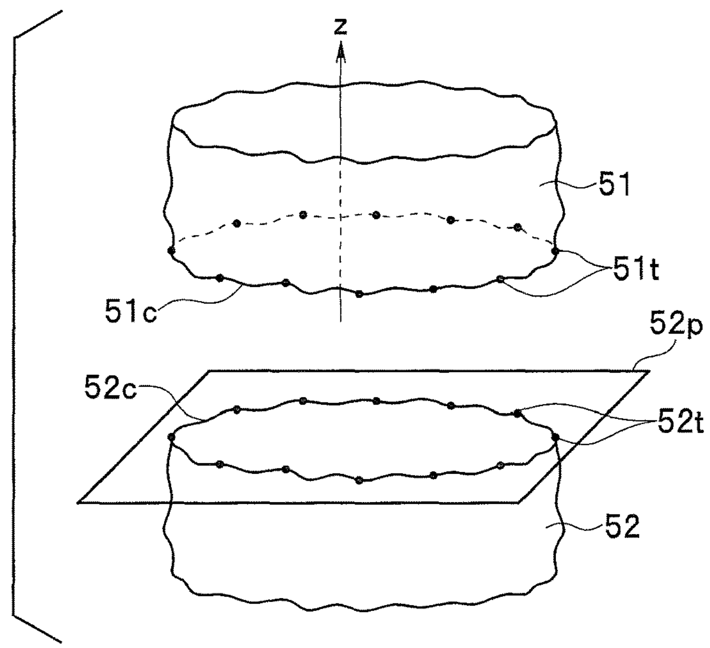
FIG. 19 is a diagram showing a state of setting a plurality of and the same number of index points on facing edges of a comparison-source partial shape and a comparison-destination partial shape in the second embodiment.

As shown in FIG. 19, the index point setting portion 31 sets a plurality of and the same number of index points 51*t* and index points 52*t* on the respective facing edges 51*c* and 52*c* of the comparison-source partial shape 51 and a comparison-destination partial shape 52, which are two different pieces of three-dimensional image data.

FIG. 19 is a diagram showing a state of setting the plurality of and the same number of index points 51*t* and index points 52*t* on the facing edges 51*c* and 52*c* of the comparison-source partial shape 51 and the comparison-destination partial shape 52.

The angle changing portion 32 rotates at least one of the comparison-source partial shape 51 and the comparison-destination partial shape 52 around the rotation axis (the z axis) so that two index points selected from the two edges 51*c* and 52*c*, respectively, may be closest to each other.

Figure 20:
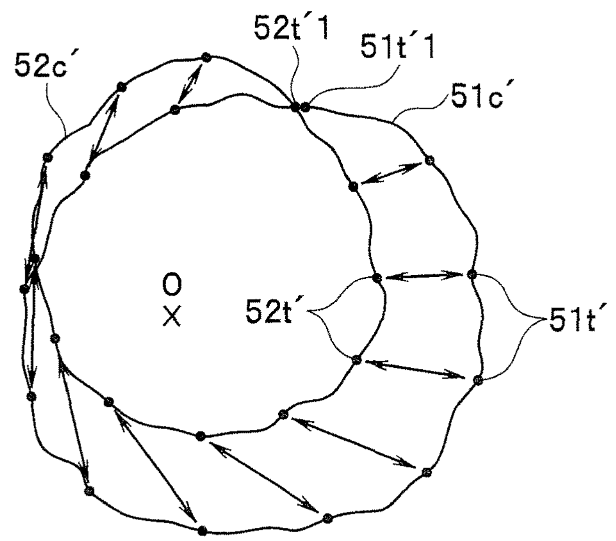
FIG. 20 is a diagram for illustrating an example of calculating an evaluation distance based on inter-index-point distances among a plurality of index points projected on a plane in the second embodiment.

As shown in FIG. 20, the evaluation distance calculating portion 33 projects to a plane 52*p* the facing edges 51*c* and 52*c* on which the index points 51*t* and the index points 52*t* are set, respectively, after the rotation by the angle changing portion 32, and calculates an evaluation distance based on distances between a plurality of index points 51*t*' and a plurality of index points 52*t*' projected on the plane 52*p*. Note that O in FIG. 20 indicates a position corresponding to the z axis that is a rotation axis.

FIG. 20 is a diagram for illustrating an example of calculating the evaluation distance based on the distances between the plurality of index points 51*t*' and the plurality of index points 52*t*' projected on the plane 52*p*.

Figure 18:
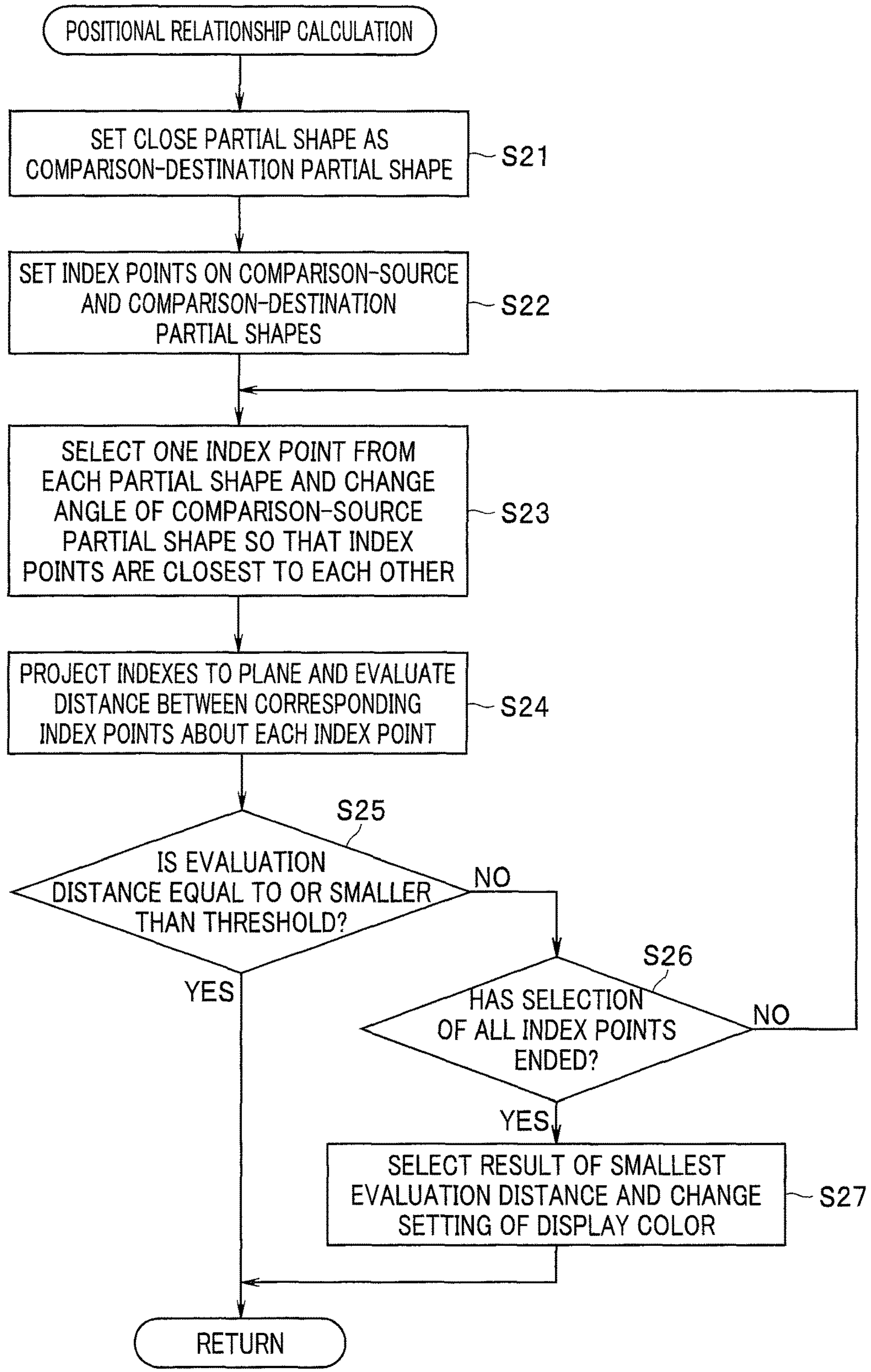
FIG. 18 is a flowchart showing a positional relationship calculating process in the image processing apparatus of the second embodiment.

FIG. 18 is a flowchart showing a positional relationship calculating process in the image processing apparatus 5.

When entering the process at step S3 in FIG. 3, the positional relationship calculating portion 23 reads out a partial shape close to the comparison-source partial shape 51 from among one or more three-dimensional shape images stored in the storage portion 25 and sets the partial shape as the comparison-destination partial shape 52 (step S21).

Next, the index point setting portion 31 sets a plurality of (for example, n) index points 51*t* on the edge 51*c* on the comparison-destination partial shape 52 side of the comparison-source partial shape 51, and sets the same number of (n) index points 52*t* on the edge 52*c* on the comparison-source partial shape 51 side of the comparison-destination partial shape 52 (step S22). The index points 51*t* and the index points 52*t* are points that divide the edge 51*c* and the edge 52*c* in n parts, respectively.

Then, the angle changing portion 32 rotates at least one of the comparison-source partial shape 51 and the comparison-destination partial shape 52, for example, the comparison-source partial shape 51 here around the z axis in three-dimensional space so that two index points selected from the two facing edges 51*c* and 52*c*, respectively, may be closest to each other (step S23).

The evaluation distance calculating portion 33 sets a plane. Here, for example, the plane 52*p* fitted to (optimized for) the edge 52*c* of the comparison-destination partial shape 52 on which the index points 52*t* are set is set. However, a plane fitted to the edge 51*c* of the comparison-source partial shape 51 on which the index points 51*t* are set may be set. The plane is not limited to the above planes, but any other plane can be set.

Then, the evaluation distance calculating portion 33 projects the facing edges 51*c* and 52*c* on which the index points 51*t* and the index points 52*t* are set, on the set plane 52*p* as edges 51*c*' and 52*c*', and calculates an evaluation distance based on distances between the plurality of index points 51*t*' and the plurality of index points 52*t*' projected on the plane 52*p* (step S24).

More specifically, the evaluation distance calculating portion 33 sets each of index point numbers of index points 51*t*'1 and 52*t*'1 on the plane 52*p* corresponding to the index points selected at step S23 to 1 and calculates a distance D (1, 1) between the index points 51*t*'1 and 52*t*'1. Then, the evaluation distance calculating portion 33 sets each of index point numbers of index points 51*t*'2 and 52*t*'2 adjoining the index points 51*t*'1 and 52*t*'1, respectively, in the same θ direction to 2 and calculates a distance D (2, 2) between the index point 51*t*'2 and 52*t*'2. Similarly, a distance D (3, 3) between index points 51*t*'3 and index points 52*t*'3 to a distance D (n, n) between index points 51*t*'n and index points 52*t*'n are calculated. Then, for example, a sum of all the distances D, σ{D(i, i)} (i=1 to n) is calculated (or, a sum of squares or the like may be calculated). Then, the calculated sum of the distances D is set as the evaluation distance. Note that, for example, a reciprocal of the evaluation distance is a similarity degree.

Then, it is judged whether or not the calculated evaluation distance is equal to or smaller than a predetermined threshold (that is, the similarity degree is equal to or higher than a predetermined threshold) (step S25).

If it is judged that the evaluation distance is not equal to or smaller than the predetermined threshold, it is judged whether all combinations between the index points 51*t* on the edge 51*c* and the index points 52*t* on the edge 52*c* have been selected or not (step S26).

If it is judged that a combination that has not been selected yet exists, the flow returns to step S23, where one index point 51*t* and one index point 52*t* are newly selected, and the process as described above is performed.

If it is judged at step S26 that all the combinations have been selected, it means that such an angle that the evaluation distance is equal to or smaller than the predetermined threshold has not been found.

In this case, a positional relationship between the comparison-source developed image 51*p* and the comparison-destination developed image 51*p*' when the smallest evaluation distance among all the calculated evaluation distances (that is, the largest similarity degree) is obtained, more specifically, the positional deviation angle Δθ around the z axis is selected, and a display color of the comparison-source partial shape 51, which is the three-dimensional image data corresponding to the comparison-source developed image 51*p*, is changed to be a color different from the comparison-destination partial shape 52 (step S27).

If the process of S27 has been performed or if it is judged at step S25 that the evaluation distance is equal to or smaller than the threshold, the flow returns to the process shown in FIG. 3 (step S4 described above).

According to the second embodiment as described above, by setting the same number of index points 51*t* and index points 52*t* on the facing edges 51*c* and 52*c* of the comparison-source partial shape 51 and the comparison-destination partial shape 52, and calculating a positional relationship based on a rotation amount when the evaluation distance based on distances between the index points 51*t*' and the index points 52*t*' projected on the plane 52*p* is equal to or smaller than a predetermined threshold, effects almost similar to effects of the first embodiment described above can be also obtained.

Note that, even if it is judged at step S25 in FIG. 18 that the evaluation distance is equal to or smaller than the threshold, the evaluation distance may be calculated by selecting all the index points. At that time, by temporarily storing a combination of index points for which the evaluation distance is judged to be equal to or smaller than the threshold, and, after evaluation distance calculation ends by selecting all the index points, selecting a positional relationship between the comparison-source developed image 51*p* and the comparison-destination developed image 51*p*' when the smallest evaluation distance among all calculated evaluation distances is obtained, it becomes possible to calculate positional relationship more accurately.

[First Modification of Second Embodiment]

Figure 21:
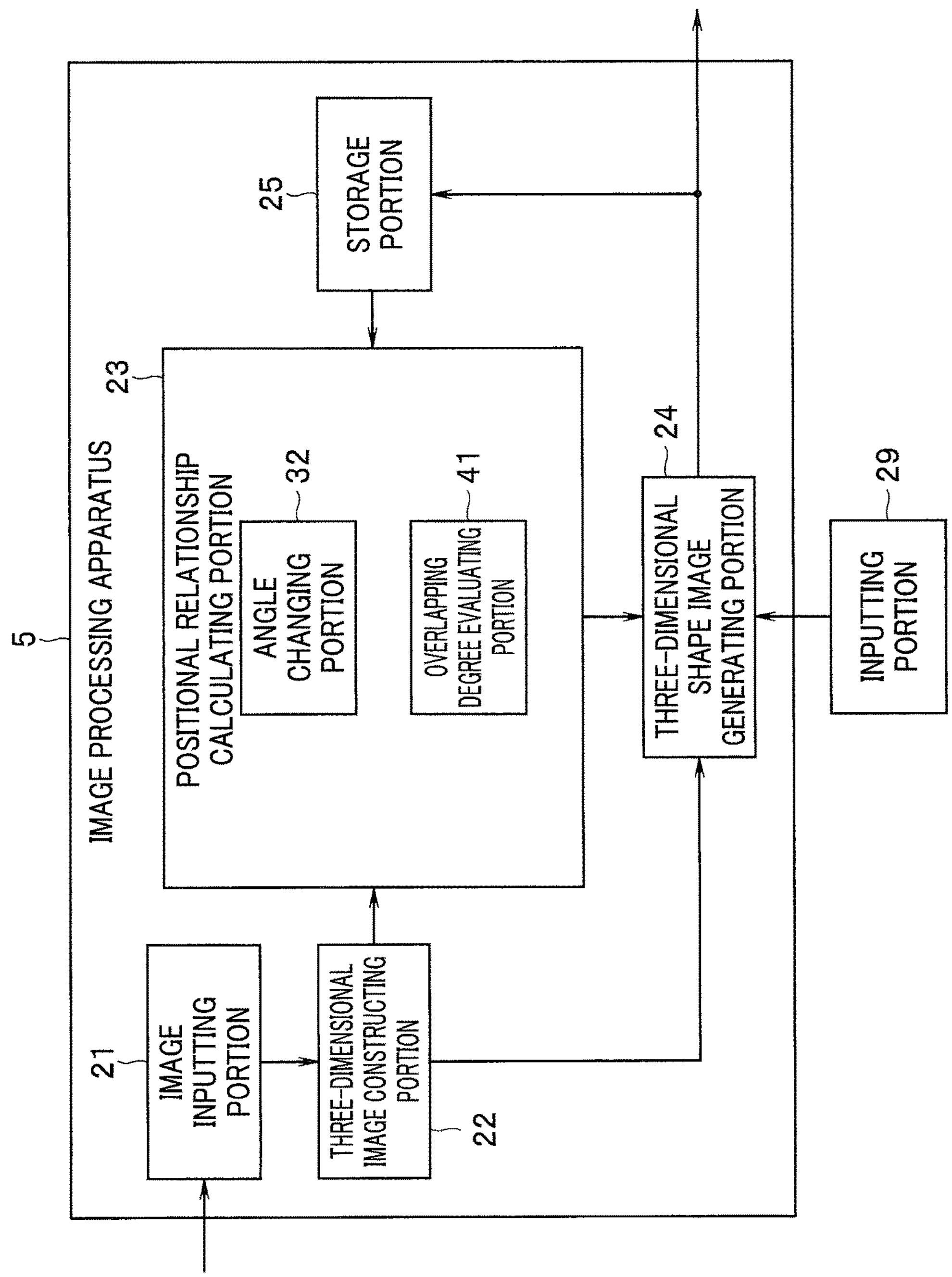
FIG. 21 is a block diagram showing a configuration of an image processing apparatus of a first modification of the second embodiment.
Figure 22:
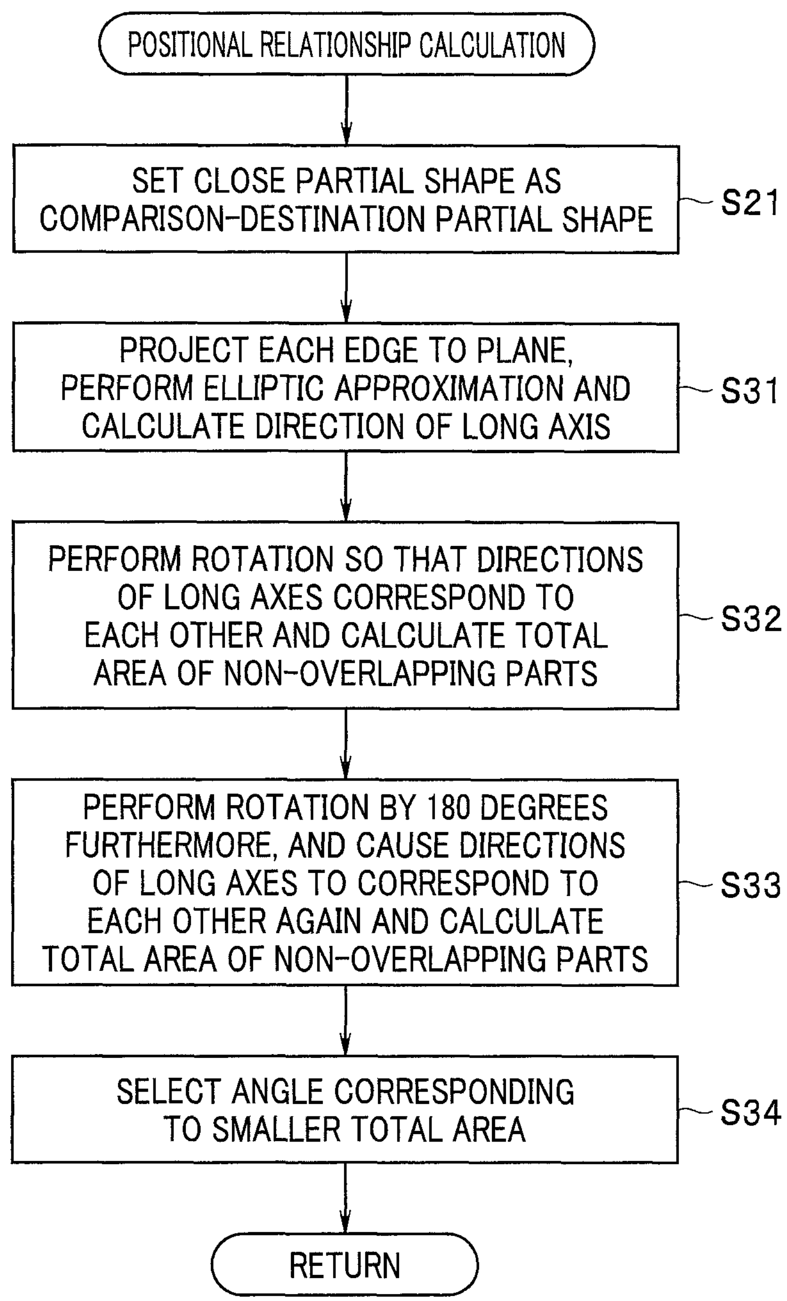
FIG. 22 is a flowchart showing a positional relationship calculating process in the image processing apparatus of the first modification of the second embodiment.
Figure 23:
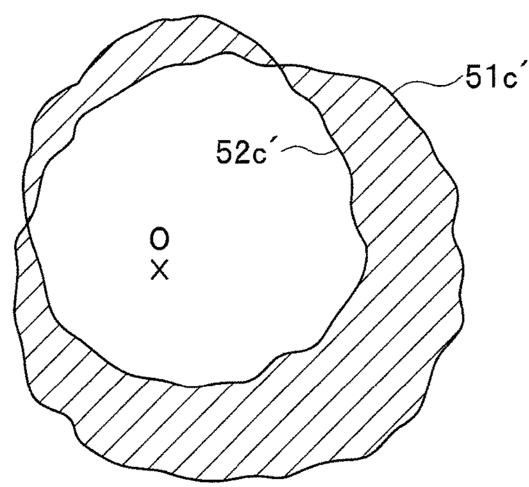
FIG. 23 is a diagram for illustrating an example of evaluating a degree of overlap between two figures surrounded by two edges projected on a plane in the first modification of the second embodiment.

FIGS. 21 to 23 show a first modification of the second embodiment of the present invention, and FIG. 21 is a block diagram showing a configuration of an image processing apparatus 5.

In the first modification of the second embodiment, as for portions similar to portions in the first and second embodiments described above, the same reference numerals will be given, and description will be appropriately omitted. Description will be made mainly on different points.

In the present first modification, a positional relationship is calculated so that the facing edges 51*c* and 52*c* of the comparison-source partial shape 51 and the comparison-destination partial shape 52 have continuity as a shape (so that the facing edges 51*c* and 52*c* may be smooth) similarly to the second embodiment described above. However, though the second embodiment is based on a distance between the edges 51*c*' and 52*c*' projected on the plane 52*p*, the present first modification is based on shapes and an overlapping area of figures surrounded by the edges 51*c*' and 52*c*' projected on the plane 52*p*.

In comparison with the image processing apparatus 5 shown in FIG. 17 of the second embodiment described above, the image processing apparatus 5 of the present first modification is different in the configuration of the positional relationship calculating portion 23.

That is, the positional relationship calculating portion 23 of the present first modification is provided with the angle changing portion 32 and an overlapping degree evaluating portion 41.

The angle changing portion 32 rotates at least one of two different pieces of three-dimensional image data around the rotation axis (the z axis).

The overlapping degree evaluating portion 41 projects to the plane 52*p* the facing edges 51*c* and 52*c* of the comparison-source partial shape 51 and the comparison-destination partial shape 52, which are the two different pieces of three-dimensional image data, and evaluates a degree of overlap between two figures surrounded by the two edges 51*c*' and 52*c*' projected on the plane 52*p* as shown in FIG. 23. FIG. 23 is a diagram for illustrating an example of evaluating the degree of overlap between the two figures surrounded by the two edges 51*c*' and 52*c*' projected on the plane 52*p*. Note that O in FIG. 23 indicates a position corresponding to the z axis that is a rotation axis.

Then, the positional relationship calculating portion 23 performs elliptic approximation of the two edges 51*c*' and 52*c*' projected on the plane 52*p*, and causes at least one of the pieces of three-dimensional image data to rotate by the angle changing portion 32 based on a rotation angle at which directions of long axes of the two approximated ellipses correspond to each other, and evaluates an overlapping degree by the overlapping degree evaluating portion 41. Then, the positional relationship calculating portion 23 calculates a positional relationship based on a rotation amount (a rotation amount of the three-dimensional image data) corresponding to a rotation angle (a rotation angle on the projection plane 52*p*) at which the overlapping degree is larger between two rotation angles at which the directions of the long axes correspond to each other (rotation angles different from each other by 180 degrees).

Next, FIG. 22 is a flowchart showing a positional relationship calculating process in the image processing apparatus 5.

When entering the process at step S3 in FIG. 3, the positional relationship calculating portion 23 performs the process of step S21 as described above and sets the comparison-destination partial shape 52.

Then, the overlapping degree evaluating portion 41 sets the plane 52*p* fitted to (optimized for) the edge 52*c* of the comparison-destination partial shape 52 similarly to the above description. However, it is possible to set other planes similarly to the above description. Then, the overlapping degree evaluating portion 41 projects the edges 51*c* and 52*c* to the set plane 52*p* as edges 51*c*' and 52*c*', performs elliptic approximation of the edge 51*c*' to calculate a direction of a long axis, and performs elliptic approximation of the edge 52*c*' to calculate a direction of a long axis (step S31).

The angle changing portion 32 calculates a rotation angle on the projection plane 52*p* at which the directions of the long axes of the two approximated ellipses correspond to each other, and calculates a rotation amount (a rotation angle around the z axis in three dimensions) of the three-dimensional image data based on the calculated rotation angle on the projection plane 52*p*. Note that though the rotation amount of the three-dimensional image data is calculated based on the rotation angle on the projection plane 52*p* here, the rotation angle on the projection plane 52*p* may be used as an approximation value of the rotation amount of the three-dimensional image data. The angle changing portion 32 causes the rotation of at least one of the comparison-source partial shape 51 and the comparison-destination partial shape 52 based on the rotation amount calculated in this way, and the overlapping degree evaluating portion 41 calculates a total area of non-overlapping parts between the figure surrounded by the edge 51*c*' and the figure surrounded by the edge 52*c*' (step S32).

After that, the angle changing portion 32 causes at least one of the comparison-source partial shape 51 and the comparison-destination partial shape 52 to rotate so that a relative rotation angle around the z axis is changed by 180 degrees (therefore, the directions of the long axes are in an inverted state relative to a state at step S32 and correspond to each other again). The overlapping degree evaluating portion 41 calculates a total area of non-overlapping parts between the figure surrounded by the edge 51*c*' and the figure surrounded by the edge 52*c*' again (step S33).

Next, the overlapping degree evaluating portion 41 compares the total area calculated at step S32 and the total area calculated at step S33 and selects a rotation angle around the z axis corresponding to the smaller total area (step S34).

If the process of step S34 has been performed, the flow returns to the process shown in FIG. 3 (step S4 described above).

Note that though in the above description a total area of non-overlapping parts is calculated twice, and a rotation angle corresponding to the smaller total area is selected, it is also possible to calculate an area of an overlapping part twice and select a rotation angle corresponding to the larger area. For example, a reciprocal of the total area (or the area of the overlapping part) is a similarity degree and shows an overlapping degree (that is, the smaller the total area is, the higher the overlapping degree is; or, the larger the area of the overlapping area is, the higher the overlapping degree is).

According to the first modification of the second embodiment as described above, by calculating a positional relationship based on shapes of the two edges 51*c*' and 52*c*' obtained by projecting the facing edges 51*c* and 52*c* of the comparison-source partial shape 51 and the comparison-destination partial shape 52 to the plane 52*p* and the degree of overlap between the two figures surrounded by the two edges 51*c*' and 52*c*', effects almost similar to the effects of the first and second embodiments described above can be obtained.

[Second Modification of Second Embodiment]

Figure 24:
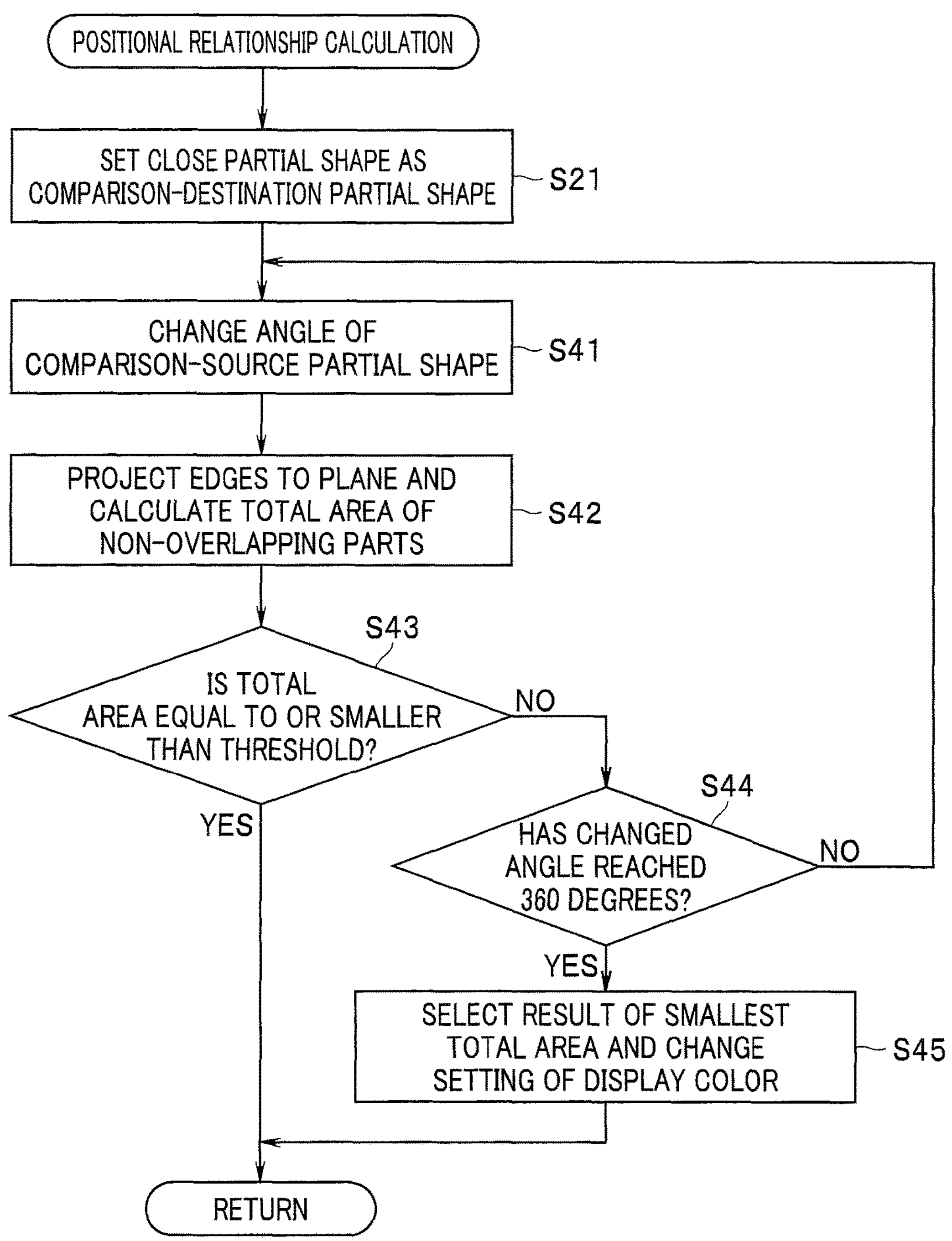
FIG. 24 is a flowchart showing a positional relationship calculating process in the image processing apparatus of a second modification of the second embodiment.

FIG. 24 shows a second modification of the second embodiment of the present invention, and FIG. 24 is a flowchart showing a positional relationship calculating process in an image processing apparatus 5.

In the second modification of the second embodiment, as for portions similar to portions in the first and second embodiments and the first modification of the second embodiment described above, the same reference numerals will be given, and description will be appropriately omitted. Description will be made mainly on different points.

In the present second modification, a positional relationship is calculated so that the facing edges 51*c* and 52*c* of the comparison-source partial shape 51 and the comparison-destination partial shape 52 have continuity as a shape (so that the facing edges 51*c* and 52*c* may be smooth) similarly to the first modification of the second embodiment described above. However, though the first modification of the second embodiment is based on shapes and an overlapping area of the figures surrounded by edges 51*c*' and 52*c*' projected on the plane 52*p*, the present second modification is based only on the overlapping area surrounded by the edges 51*c*' and 52*c*' projected on the plane 52*p*.

A configuration of the image processing apparatus 5 of the present second modification is similar to the configuration of the first modification of the second embodiment shown in FIG. 21.

However, the positional relationship calculating portion 23 of the present second modification does not perform elliptic approximation or calculation of long-axis directions, but evaluates an overlapping degree by the overlapping degree evaluating portion 41 while rotating at least one of pieces of three-dimensional image data by the angle changing portion 32 and calculates a positional relationship based on a rotation amount when it is shown that the overlapping degree is equal to or higher than a predetermined threshold.

Next, a positional relationship calculating process in the image processing apparatus 5 will be described with reference to FIG. 24.

When entering the process at step S3 in FIG. 3, the positional relationship calculating portion 23 performs the process of step S21 as described above to set the comparison-destination partial shape 52.

Then, the angle changing portion 32 rotates at least one of the comparison-source partial shape 51 and the comparison-destination partial shape 52, for example, the comparison-source partial shape 51, here by a predetermined rotation angle $\Delta\theta$ around the z axis in three-dimensional space (step S41).

Note that if an initial value when step S41 is executed first is indicated by $\phi$, and the number of loops from step S41 to step S44 to be described later is indicated by n, the rotation angle of the comparison-source partial shape 51 is sequentially changed as shown by $\phi+\Delta\theta\times n$.

The overlapping degree evaluating portion 41 sets the plane 52*p* fitted to (optimized for) the edge 52*c* of the comparison-destination partial shape 52 similarly to the above. However, just as the above, it is possible to set other planes. Then, the overlapping degree evaluating portion 41 projects the edges 51*c* and 52*c* to the set plane 52*p* as edges 51*c*' and 52*c*', and calculates a total area of non-overlapping parts between a figure surrounded by the edge 51*c*' and a figure surrounded by the edge 52*c*' (step S42).

Note that though the total area of the non-overlapping parts is calculated, and a process shown below is performed here, a similar process can be also performed when an area of an overlapping part is calculated as described above.

Next, the overlapping degree evaluating portion 41 judges whether or not the total area is equal to or smaller than a predetermined threshold (that is, whether or not the overlapping degree is equal to or higher than a predetermined threshold, or whether or not the similarity degree is equal to or higher than a predetermined threshold) (step S43).

If it is judged that the total area is larger than the predetermined threshold, the positional relationship calculating portion 23 judges whether an angle changed by the angle changing portion 32 has reached 360 degrees or not (step S44). If the changed angle has not reached 360 degrees, the flow returns to step S41, where the angle is changed by the angle changing portion 32, and the process as described above is performed.

If it is judged at step S44 that the changed angle has reached 360 degrees, it means that an angle at which the total area is equal to or smaller than the predetermined threshold has not been found.

In this case, a positional relationship between the edge 51*c*' of the comparison-source partial shape 51 and the edge 52*c*' of the comparison-destination partial shape 52 when the smallest total area among all the calculated total areas (that is, the highest similarity degree) is obtained, more specifically, a positional deviation angle $\phi+\Delta\theta\times n$ around the z axis is selected, and a display color of the comparison-source partial shape 51, which is three-dimensional image data corresponding to the comparison-source developed image 51*p*, is changed to be a color different from the comparison-destination partial shape 52 (step S45).

If the process of S45 has been performed or if it is judged at step S43 that the total area is equal to or smaller than the threshold, the flow returns to the process shown in FIG. 3 (step S4 described above).

According to the second modification of the second embodiment as described above, by calculating a positional relationship based on a rotation amount when it is shown that a degree of overlap between the two figures surrounded by the two edges 51*c*' and 52*c*' obtained by projecting the facing edges 51*c* and 52*c* of the comparison-source partial shape 51 and the comparison-destination partial shape 52 to the plane 52p is equal or higher than a predetermined threshold, effects almost similar to the effects of the first and second embodiments described above can be obtained. Further, it can be expected that the calculated positional relationship is more accurate than the first modification of the second embodiment described above. Note that even if it is judged at step S43 in FIG. 23 that the total area is equal to or smaller than the threshold, the total area may be calculated until the changed angle reaches 360 degrees. At that time, by temporarily storing a changed angle at which the total area is equal to or smaller than the threshold, and after the total area is calculated until the changed angle reaches 360 degrees, selecting a positional relationship between the comparison-source developed image 51p and the comparison-destination developed image 51p' when the smallest total area among all calculated total areas is obtained, it becomes possible to calculate a more accurate positional relationship.

Note that though embodiments using a 5D sensor have been described in the present document, the present invention is not limited to the embodiments. For example, in the case of using a 6D sensor, since information about rotational degree of freedom around an axis in an image pickup direction can be further acquired (therefore, all information about rotational degrees around three coordinate axes for describing a three-dimensional translational degree of freedom can be acquired), it becomes easier for the three-dimensional shape image generating portion to perform the process for arranging different pieces of three-dimensional image data in three-dimensional space than the case of using a 5D sensor. However, since noise overlaps with the degree-of-freedom information measured by the 6D sensor, a slight deviation may occur at the time of arranging the different pieces of three-dimensional image data in the three-dimensional space. Even in such a case, by applying the above-described template matching and the selection of a positional relationship based on an evaluation distance to the process for arranging the pieces of three-dimensional image data in the three-dimensional space, it becomes possible to realize more accurate calculation of a positional relationship.

Note that each portion described above may be configured as a circuit. The arbitrary circuit may be implemented as a single circuit or may be implemented by a combination of a plurality of circuits as long as the same function can be achieved. The arbitrary circuit is not limited to being configured as a dedicated circuit for achieving an intended function. A configuration is also possible in which the intended function is achieved by causing a general-purpose circuit to execute a processing program.

Though description has been made above mainly on an image processing apparatus and an image processing system, an operation method for causing the image processing apparatus or the image processing system to operate as described above is also possible. A processing program for causing a computer to perform a process similar to the process of the image processing apparatus or the image processing system, a computer-readable non-transitory recording medium in which the processing program is recorded and the like are also possible.

The present invention is not limited to the embodiments described above as the embodiments are. The components can be modified and embodied within a range not departing from the spirit of the invention at an implementation stage. Further, by appropriate combinations of a plurality of components disclosed in each of the above embodiments, various aspects of the invention can be formed. For example, some components may be deleted from all the components shown in each embodiment. Components among different embodiments may be combined. Thus, it goes without saying that various modifications and applications are possible within the range not departing from the spirit of the invention.

What is claimed is:

1. An image processing apparatus comprising a processor including hardware, wherein the processor is configured to:

receive a two-dimensional subject image obtained by picking up an image of a subject, and a piece of image pickup position information including three-dimensional xyz coordinates of an endoscope distal end portion when the subject image is picked up and rotation angles around an x axis and a y axis perpendicular to a z axis, where the z axis is an optical axis of an objective lens mounted on an endoscope insertion portion;

construct a first piece of three-dimensional image data showing a three-dimensional shape of a first area of the subject and a second piece of three-dimensional image data showing a three-dimensional shape of a second area of the subject, based on two different subject images, where each of the subject images is the subject image described above;

arrange the three-dimensional shape of the first area included in the first piece of three-dimensional image data and the three-dimensional shape of the second area included in the second piece of three-dimensional image data at positions corresponding to respective pieces of image pickup position information where each of the pieces of image pickup position information is the piece of image pickup position information described above, and calculate a deviation angle indicating an amount of angle deviation around a rotation axis, where the rotation axis is in an image pickup direction of the subject images determined based on the pieces of image pickup position information, based on at least one of a degree of similarity between pieces of hue information that the respective pieces of three-dimensional image data include, a degree of similarity between pieces of texture information that the respective pieces of three-dimensional image data include, and a degree of similarity between pieces of information about edges showing shapes of facing parts of the three-dimensional shapes of the first area and the second area; and correct the deviation angle between the three-dimensional shapes of the first area and the second area arranged at positions corresponding to the respective pieces of image pickup position information and arrange the three-dimensional shapes in three-dimensional space to generate a three-dimensional shape image.

2. The image processing apparatus according to claim 1, wherein the processor is configured to generate the three-dimensional shape image arranged in the three-dimensional space by rotating at least one of the three-dimensional shapes so that an amount of the deviation around the rotation axis between the three-dimensional shapes of the first area and the second area is minimized, based on the calculated deviation angle.

3. The image processing apparatus according to claim 1, wherein the processor is configured to:

detect a characteristic part from one of the two different pieces of three-dimensional image data based on a predetermined parameter for the pieces of hue information or the pieces of texture information;

divide the other of the two different pieces of three-dimensional image data into a plurality of areas and calculate the degree of similarity between each of the areas and the detected characteristic part; and calculate the deviation angle when the calculated degree of similarity is equal to or higher than a predetermined threshold.

4. The image processing apparatus according to claim 3, wherein the processor is configured to:

generate two peripheral images of the subject by two-dimensionally developing the two different pieces of three-dimensional image data, respectively; and detect the characteristic part based on the predetermined parameter of one of the two peripheral images.

5. The image processing apparatus according to claim 3, wherein for one of the two different pieces of three-dimensional image data, the processor is configured to detect a part where an amount of luminance value change as the predetermined parameter for the pieces of texture information is equal to or larger than a second threshold, as the characteristic part.

6. The image processing apparatus according to claim 1, wherein the processor is configured to:

calculate the deviation angle based on the degree of similarity between the pieces of information about the edges showing the shapes of the facing parts of the three-dimensional shapes of the first area and the second area;

set a plurality of and a same number of index points on each of the two edges;

rotate at least one of the three-dimensional shapes of the first area and the second area around the rotation axis so that two index points selected from the two edges, respectively, are closest to each other;

project to a plane the facing edges where the index points are set and calculate an evaluation distance based on inter-index-position distances among the plurality of index points projected on the plane; and calculate the evaluation distance while rotating at least one of the three-dimensional shapes of the first area and the second area, changing each of the two index points to be selected, and calculate the deviation angle based on a rotation amount when the evaluation distance at which the shapes of the facing edges become similar is equal to or smaller than a predetermined threshold.

7. The image processing apparatus according to claim 1, wherein the processor is configured to:

calculate the deviation angle based on the degree of similarity between the pieces of information about the edges showing the shapes of the facing parts of the three-dimensional shapes of the first area and the second area;

rotate at least one of the three-dimensional shapes of the first area and the second area around the rotation axis;

project the two edges to a plane and evaluate a degree of overlap between two figures surrounded by the two edges projected on the plane; and evaluate the degree of overlap while rotating at least one of the three-dimensional shapes of the first area and the second area, and calculate the deviation angle based on a rotation amount when the degree of overlap at which the shapes of the facing edges become similar is equal to or higher than a predetermined threshold.

8. An image processing system comprising:

an endoscope configured to pick up an image of a subject and generate a two-dimensional subject image; and the image processing apparatus according to claim 1, wherein the two-dimensional subject image received by the processor is the two-dimensional subject image generated by the endoscope.

9. A non-transitory computer-readable storage medium storing instructions that cause a computer to at least perform:

receiving a two-dimensional subject image obtained by picking up an image of a subject, and a piece of image pickup position information including three-dimensional xyz coordinates of an endoscope distal end portion when the subject image is picked up and rotation angles around an x axis and a y axis perpendicular to a z axis, where the z axis is an optical axis of an objective lens mounted on an endoscope insertion portion;

constructing a first piece of three-dimensional image data showing a three-dimensional shape of a first area of the subject and a second piece of three-dimensional image data showing a three-dimensional shape of a second area of the subject, based on two different subject images, where each of the subject images is the subject image described above;

arranging the three-dimensional shape of the first area included in the first piece of three-dimensional image data and the three-dimensional shape of the second area included in the second piece of three-dimensional image data at positions corresponding to respective pieces of image pickup position information, where each of the pieces of image pickup position information is the piece of image pickup position information described above, and calculating a deviation angle indicating an amount of angle deviation around a rotation axis, where the rotation axis is in an image pickup direction of the subject images determined based on the pieces of image pickup position information, based on at least one of a degree of similarity between pieces of hue information that the respective pieces of three-dimensional image data include, a degree of similarity between pieces of texture information that the respective pieces of three-dimensional image data include, and a degree of similarity between pieces of information about edges showing shapes of facing parts of the three-dimensional shapes of the first area and the second area; and correcting the deviation angle between the three-dimensional shapes of the first area and the second area arranged at positions corresponding to the respective pieces of image pickup position information, and arranging the three-dimensional shapes in three-dimensional space to generate a three-dimensional shape image.

* * * * *